United States Patent

(12) United States Patent
Bowman et al.

(10) Patent No.: US 9,254,367 B2
(45) Date of Patent: *Feb. 9, 2016

(54) INHALER 624

(71) Applicant: AstraZeneca AB, Södertälje (SE)

(72) Inventors: Nicholas Bowman, Harston (GB); Jörgen Fruensgaard, Struer (DK); Jörgen Funder Rasmussen, Struer (DK); Henrik Hougaard Vilstrup, Streur (DK); Keld Sloth Christensen, Streur (DK)

(73) Assignee: ASTRAZENECA AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/315,625

(22) Filed: Jun. 26, 2014

(65) Prior Publication Data

US 2015/0122249 A1 May 7, 2015

Related U.S. Application Data

(63) Continuation of application No. 13/450,804, filed on Apr. 19, 2012, now Pat. No. 8,800,559, which is a continuation of application No. 11/962,860, filed on Dec. 21, 2007, now Pat. No. 8,225,790.

(60) Provisional application No. 60/883,076, filed on Jan. 2, 2007.

(51) Int. Cl.
*A61M 11/00* (2006.01)
*A61M 15/00* (2006.01)

(52) U.S. Cl.
CPC .......... *A61M 15/0091* (2013.01); *A61M 15/007* (2014.02); *A61M 15/008* (2014.02);
(Continued)

(58) Field of Classification Search
CPC .......... A61M 15/009; A61M 15/0091; A61M 15/00; A61M 15/0026; A61M 2205/6072; A61M 2205/6081; A61M 15/007; A61M 15/008; A61M 15/0095; A61M 15/0025; A61M 15/0071; A61M 15/0086

USPC ............ 128/204.26, 200.14, 200.18, 200.23, 128/204.18, 203.12; 239/337, 338

See application file for complete search history.

(56) References Cited

U.S. PATENT DOCUMENTS 5,027,808 A   7/1991   Rich et al.
5,031,610 A   7/1991   Armstrong et al.
(Continued)

FOREIGN PATENT DOCUMENTS

CN   1320057 A   10/2001
GB   2 263 873 A   8/1993
(Continued)

OTHER PUBLICATIONS

International Search Report issued in PCT Application No. PCT/SE2008/000005, mailed on Feb. 25, 2008.
(Continued)

*Primary Examiner* — Steven Douglas
(74) *Attorney, Agent, or Firm* — Finnegan, Henderson, Farabow, Garrett & Dunner, LLP

(57) ABSTRACT

In an exemplary embodiment, a breath actuated inhaler (BAI) actuator may include a loading element capable of being loaded with an actuation force and a breath actuated trigger mechanism arranged to counteract the actuation force of the loading element and to fire the actuator by releasing the actuation force of the loading element in response to an inhalation breath. An actuation locking device may be moveable between a locked position wherein it relieves the actuation force from the trigger mechanism setting the trigger mechanism in a neutral position, and an armed position wherein the trigger mechanism is set in an armed position.

18 Claims, 20 Drawing Sheets

(52) U.S. Cl.
CPC ......... *A61M15/009* (2013.01); *A61M 15/0025* (2014.02); *A61M 15/0026* (2014.02); *A61M 15/0071* (2014.02); *A61M 15/0086* (2013.01); *A61M 15/0095* (2014.02); *A61M 2205/6072* (2013.01); *A61M 2205/6081* (2013.01)

(56) References Cited

U.S. PATENT DOCUMENTS

| | | | |
|---|---|---|---|
| 5,623,920 | A | 4/1997 | Bryant |
| 6,439,227 | B1 | 8/2002 | Myrman et al. |
| 7,575,003 | B2 | 8/2009 | Rasmussen et al. |
| 2002/0073996 | A1 | 6/2002 | O'Leary |
| 2002/0100472 | A1 | 8/2002 | Casper et al. |
| 2003/0116155 | A1 | 6/2003 | Rasmussen |
| 2006/0243275 | A1 | 11/2006 | Ruckdeschel et al. |

FOREIGN PATENT DOCUMENTS

| | | |
|---|---|---|
| JP | 2003-527221 A | 9/2003 |
| JP | 2005-506882 A | 3/2005 |
| RU | 2077893 C1 | 4/1997 |
| WO | WO 92/07599 A1 | 5/1992 |
| WO | WO 92/10229 A1 | 6/1992 |
| WO | WO 00/16836 A1 | 3/2000 |
| WO | WO 01/70313 A1 | 9/2001 |
| WO | WO 01/70316 A1 | 9/2001 |
| WO | WO 02/26301 A1 | 4/2002 |
| WO | WO 03/035155 A1 | 5/2003 |
| WO | WO 2006/115732 A2 | 11/2006 |
| WO | WO 2008/082359 A1 | 7/2008 |

OTHER PUBLICATIONS

Written Opinion issued in PCT Application No. PCT/SE2008/000005, mailed Feb. 25, 2008.

INHALER 624

RELATED APPLICATIONS

This application is a continuation of U.S. Pat. No. 8,800,559, filed on Apr. 19, 2012, which claims the benefit of priority to U.S. Pat. No. 8,225,790, filed Dec. 21, 2007, which claims the benefit of prior U.S. Provisional Application No. 60/883,076, filed Jan. 2, 2007, each of which is herein incorporated by reference in its entirety.

TECHNICAL FIELD

The present invention relates to an inhaler for delivery of a medicament by inhalation and in particular to the actuation mechanism used in the inhaler to actuate a canister to dispense a dose of medicament.

BACKGROUND OF THE INVENTION

Inhalers are commonly used for delivery of a wide range of medicaments. The inhaler holds a canister of medicament, the canister being actuated e.g. by compression to deliver a dose of medicament through a mouthpiece to a user. The inhaler may be provided with an actuation mechanism to actuate the canister automatically and thus dispense a dose of medicament. Some known actuation mechanisms are breath-actuated, so that they operate in response to inhalation by a user. This ensures that a dose of medicament dispensed on actuation of the canister is supplied whilst the user is inhaling. This is particularly useful for those users who may find it difficult to co-ordinate the dispensing of a dose of medicament, by for example, the actuation of a button, with inhaling the dose.

A known breath-actuated inhaler has an actuation mechanism operable by compression of a canister of medicament to deliver a dose of medicament in response to inhalation by a user. The actuation mechanism comprises a loading mechanism to bias compression of the canister. A triggering mechanism holds the loading mechanism against compression of the canister. When delivery of a dose of medicament is required, the triggering mechanism releases to allow compression of the canister in response to inhalation by the user. An actuating means is connected to a cover for the mouthpiece and is responsive to the closing movement of the cover for re-setting the actuation mechanism. Such an arrangement results in the components of the trigger mechanism not being loaded when the inhaler is not in use. When the cover is closed, critical force is redirected from the triggering mechanism during storage (cap closed). Over time, loading of critical components can quicken the onset of material creep, resulting in mechanical failure of the inhaler and its subsequent inability to deliver a dose of medicament after a number of uses. This situation can be extremely dangerous for the user in an emergency when it is vital that the inhaler deliver a dose when required.

SUMMARY OF THE INVENTION

It is, for reasons mentioned above, an object of the present invention to provide an inhaler incorporating such an actuation mechanism to alleviate the problems described above.

Accordingly, there is provided a breath actuated inhaler (BAI) actuator, comprising:
a loading element capable of being loaded with an actuation force,
a breath actuated trigger mechanism arranged to counteract the actuation force of the loading element, and to fire the actuator by releasing the actuation force of the loading element in response to an inhalation breath, and
actuation locking means moveable between a locked position wherein it relieves the actuation force from the trigger mechanism setting the trigger mechanism in a neutral position, and an armed position wherein the trigger mechanism is set in an armed position.

In this way, components of the trigger mechanism and finely toleranced parts are not loaded at any time, either when the inhaler is reset or discharged, except for when the actuator is armed and ready to deliver a dose of medicament. By avoiding heavy loading of the trigger mechanism, the onset of material creep is significantly reduced, resulting in an inhaler that may be re-used more safely.

Preferably, the loading means further loads the canister with an actuation force for compression of the canister from a rest position to the charging position. Movement of the activating means to the first position applies a force directly to the loading means to compress the canister from the rest position to the charging position. By providing such an arrangement, the canister may be pre-compressed thus reducing the mechanical shock prior to the compressing of the canister to deliver a dose of medicament.

Preferably, movement of the actuating means between the first position and the second position applies a force directly to the loading means in a direction substantially along the cylindrical axis of the canister.

Preferably, the loading means comprises a resilient loading element arranged to be loaded with an actuation force, the resilient loading element being arranged when loaded to bias compression of the canister. Typically, the resilient loading element is in a loaded state in which the resilient loading element stores the actuation force.

The resilient loading element may be a coiled plastic or metal spring. However, alternative arrangements may be envisaged that are able to store and release an actuation force, such as compressed air, a tension spring, an electric motor etc.

Preferably, the trigger mechanism comprises a lever member and a lever lock member, the lever lock member having a locked position and being so arranged as to hold the lever member in a locked position to hold loading means against compression of the canister.

Preferably, the latch means comprises a trigger element and a droplink element, movement of the trigger element to its latch release position causes movement of the droplink element to its latch release position, thereby moving the lever lock from its lock position to a release position, causing the lever to move from its locked position to a release position thereby allowing compression of the canister to release a dose of medicament. The droplink element may further comprise a re-set position. This enables the droplink element to readily take up its latch position.

Alternatively, the trigger element is arranged to be moved to the unlatched position by the application of a manual action by the user into the latch release position described above. For example, a firing button may be provided for manual depression by the user which serves to contact the trigger element to move the trigger element.

Preferably, the actuation mechanism is breath-actuated, the trigger element being arranged to be moved to the latch release position by inhalation at the mouthpiece to cause operation of the actuation mechanism. The trigger element may be an inhalation responsive trigger vane.

Preferably, the actuating means is mounted for pivotal movement to apply a force directly to a yoke. The actuating means may be a protective cover or cap (see comment on page 2).

BRIEF DESCRIPTION OF THE DRAWINGS

To allow a better understanding, embodiments of the present invention will now be described, by way of non-limitative examples only, with reference to the accompanying drawings, in which.

DETAILED DESCRIPTION OF PREFERRED EMBODIMENTS

Figure 1:
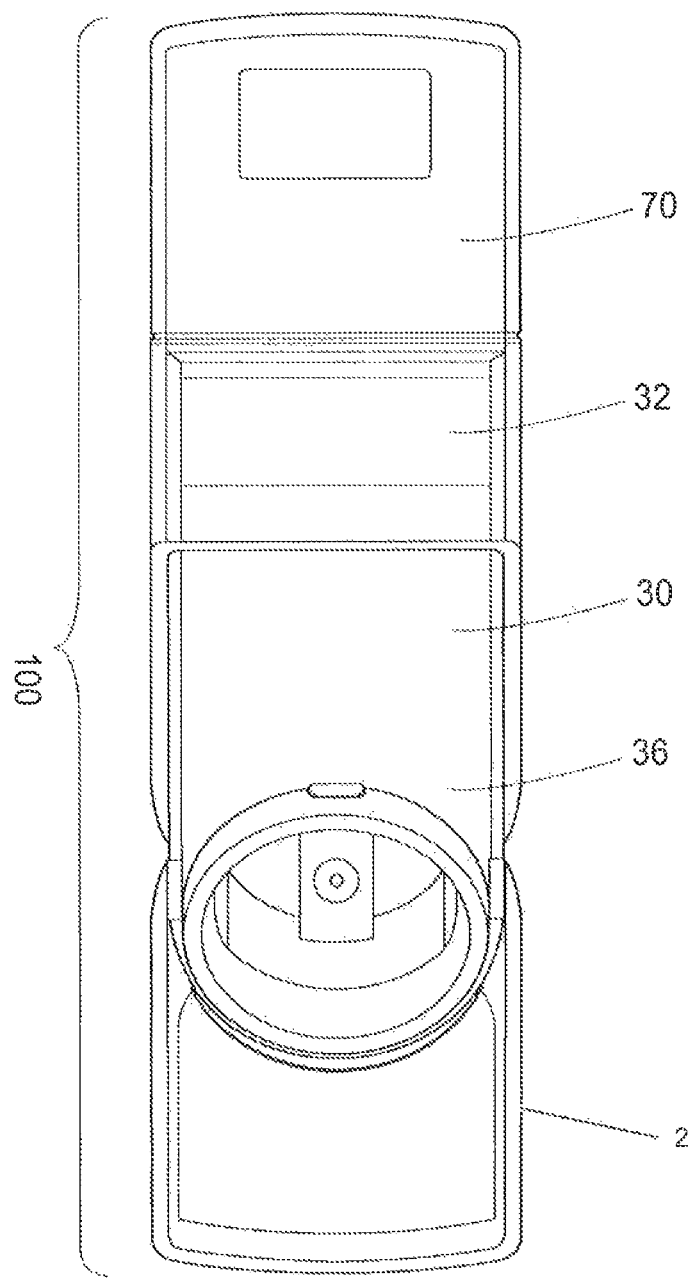
FIG. 1 is a front perspective view of one embodiment of an inhaler with the actuating means in the open position.
Figure 1A:
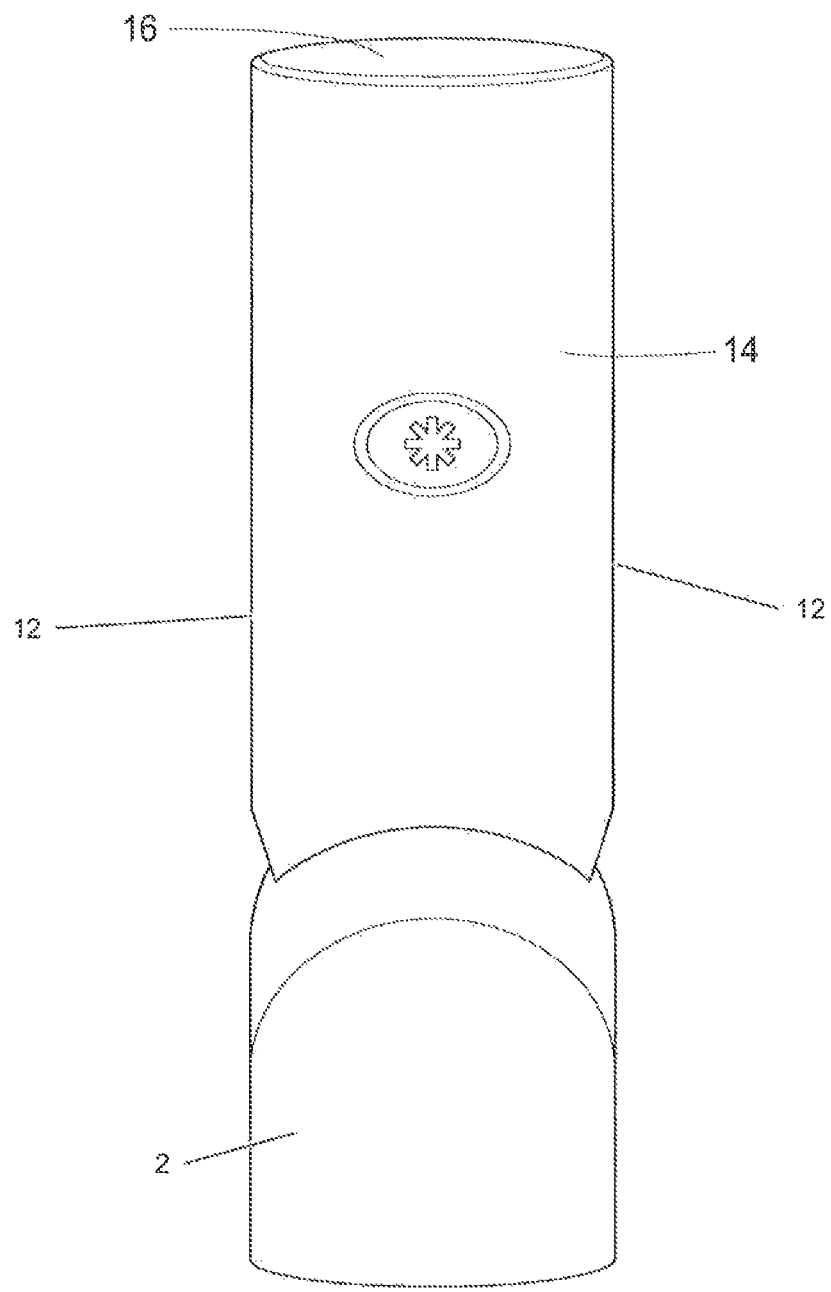
FIG. 1a is a rear perspective view of the inhaler of FIG. 1 with the actuating means in the open position.

Referring now to FIGS. 1, 1a, 2 and 7, one embodiment of a breath actuated inhaler (BAI) actuator 100, with respect to this embodiment referred to as an inhaler 100, has a housing 10 comprising side walls 12, a rear wall 14 and a top wall 16. The rear wall 14 forms a curved surface to facilitate comfortable receipt of the inhaler 100 in the palm of the user's hand. The walls 12, 14, 16 of the housing 10 define a space for accommodating a canister 20 of medicament in a chassis 40, and an actuation mechanism 1 so operable as to actuate the canister 20 to deliver a dose of medicament. The chassis 40 retains most of the mechanical components of the inhaler 100 in the correct position, and is heavily loaded. For example, most of the components of the trigger mechanism are pivoted on the chassis 40, thus reducing problems caused by tolerance. The front opening in the housing 10 accommodates a registration module (electronic module) 70 and an upper portion 32 of a facia 30, each having opposed side walls 34, respectively to fit flush with the side walls 12 of the housing 10.

A mouthpiece 60 protrudes from the housing 10 and may be protected from damage and/or the entering of foreign bodies e.g. dust by locking or actuating means 2 pivotally mounted for movement on the chassis 40 as illustrated. In the embodiment shown, the actuating means is a protective cover 2 and shall now be referred to as such. The cover 2 has opposed side walls to fit flush with the side walls of the housing 10, and a rear curved wall to fit flush with the rear wall of the housing 10. The rear walls of the respective housing and the cover together form a curved surface to facilitate comfortable receipt of the inhaler 100 in the palm of the user's hand.

Figure 3:
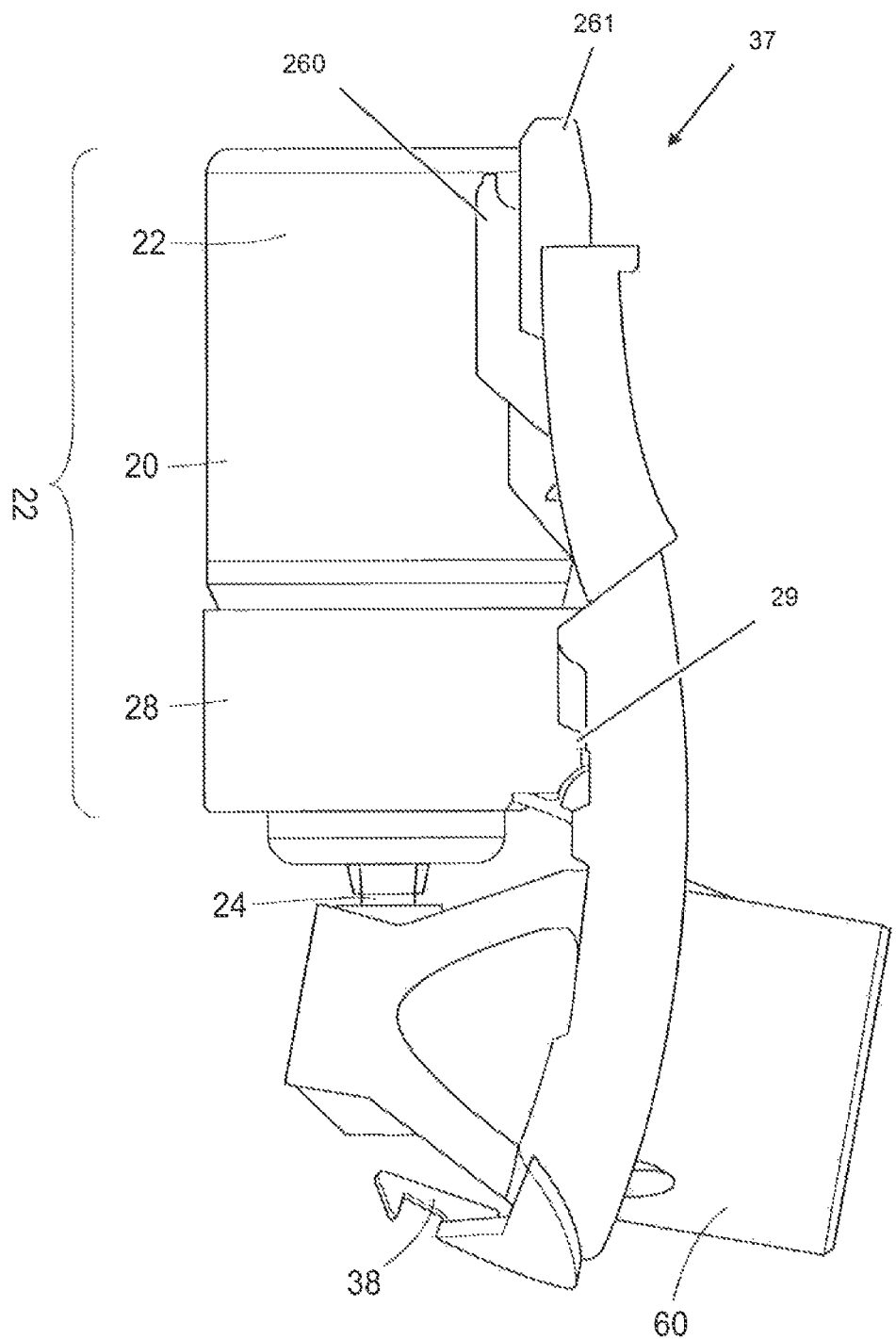
FIG. 3 is a side view of the canister module removed from the inhaler of FIG. 1.
Figure 3A:
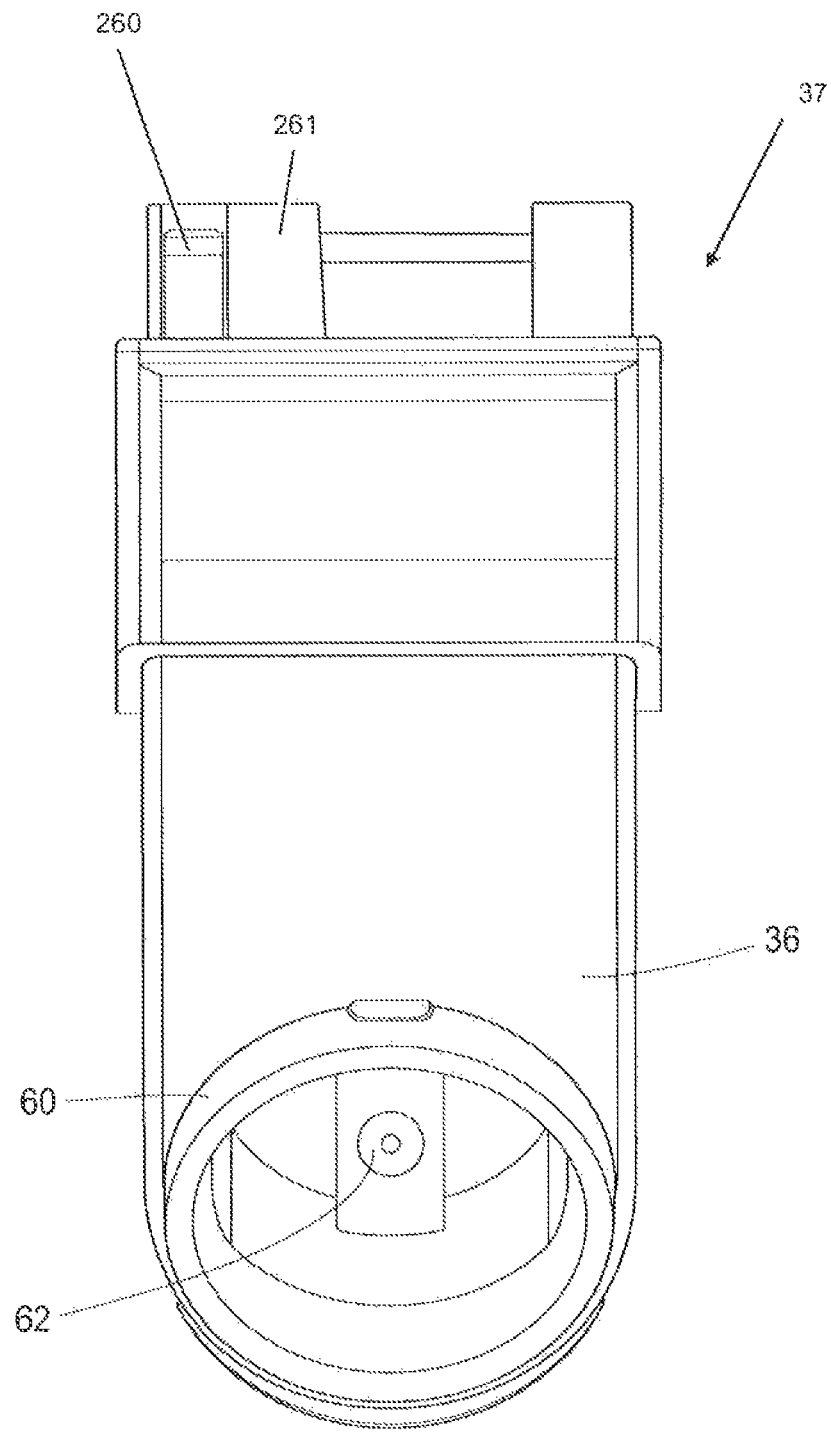
FIG. 3a is a front perspective view of the canister module removed from the inhaler of FIG. 1.

The canister 20 fits in the chassis 40 retained in the housing 10 and may be slidably removed for replacement as illustrated in FIGS. 3 and 3a. The canister 20 is of a known type for holding a suspension or solution of a medicament in a propellant under pressure. The canister 20 comprises a generally cylindrical body 22 and a valve stem 24 which are compressible together to deliver a dose of medicament from the valve stem 24. The canister 20 includes a metering chamber (not shown), which captures a defined volume of medicament from the body 22 of the canister 20, which volume of medicament is delivered as a metered dose from the valve stem 24 on compression of the valve stem relative to the body 22. The valve stem 24 is biased outwardly to reset the canister 20 after compression for refilling the metering chamber. The valve stem 24 is located in a nozzle block 62. The nozzle block 62 is formed as part of, and in open communication with, the mouthpiece 60 to direct a dose of medicament delivered from the valve stem 24 out of the inhaler 100 through the mouthpiece 60.

An opening in the lower part 36 of the facia 30 is so sized and shaped as to receive the mouthpiece 60, which is of a corresponding size and shape. According to one embodiment, there is provided a replaceable canister module 37 comprising a canister 20 and a mouth piece 60 with a nozzle block 62, wherein the canister body 22 is moveable in the actuation direction with respect to the nozzle block 62, and wherein the canister module 37 is inserted in the actuator 10 in a direction essentially transverse to the actuation direction of the canister. The canister 20 is moveably connected to, and supported by, the facia 30 and the mouth piece 60, by a collar 28 fitted around a necked portion of the canister body 22. The collar 28 may be permanently fixed to the canister 20, and comprises a connection member 29 that enables a linear motion of the canister 20 in the actuation direction with respect to the facia 30 and mouthpiece 60. This allows actuation of the canister by compression of the canister body towards the valve stem when the stem is fixed relative to the inhaler in the nozzle block. In the disclosed embodiment, the collar 28 has a notched/'keyed' inner surface engaging the crimp joining the canister 20 and valve. In other embodiments, the canister 20 may be interconnected with the facia 30 and the mouthpiece 60 in another way. The canister 20 may be integral with the facia and the mouthpiece 60 such that the facia and mouthpiece 60 are removed from the housing and inserted into the housing together with the canister 20 as a canister module 37 as illustrated in FIGS. 3 and 3a. When such a canister module 37 is inserted into the housing, the mouthpiece 60 stands on a platform in the chassis and encloses the airflow. The mouthpiece 60 forms the end of an air passage through the housing, the inlet of the air passage being adjacent a trigger element. A clip 38 retains the facia to the housing. The canister and collar have a small degree of movement along the axis of the canister to allow actuation of the canister.

The outer surface of the upper portion of the facia 30 carries an indication of the type of medicament in the canister 20 to which the facia 30 is connected. The indication may be printed information, an embossed or indented pattern, for example, Braille, or the colour of the facia.

The registration module 70 is responsive to firing of the actuator 100. According to one embodiment the registration module 70 is arranged to detect the presence of a canister module 37 in the actuator, and arranged to disregard firings of the actuator when no 2n canister module 37 is present. The detection of a canister module 37 may e.g. be performed by a microswitch (not shown) that is activated when a canister module 37 is inserted into the actuator, eg. by detection of a tab 261 extending from the canister module for interaction with said microswitch. According to one embodiment, the canister module 37 comprises a non-use indicator 260 that is preset in a non-use state and which is set in an irreversible in-use state at the first actuation of the canister module 37. According to one embodiment, the non-use indicator 260 is a moveable tab, that initially in its non-use state is hidden from detection by the registration module 70, and upon the first actuation (use) is moved to an exposed "in-use state" where the registration module 70 detects the presence of the tab. When, the moveable tab has entered the in-use state it is mechanically hindered from returning to its non-use state. Preferably, the moveable tab is hindered from being returned to its non-use mode by tamper proof means. The registration module 70 is arranged to detect the state of the of the non-use indicator 260, e.g. by a second microswitch, each time a canister module 37 is arranged in the actuator, and in response to a:

non-use state; initiate a new actuation counting cycle, and
in-use state; not count actuations.

As is evident to any person skilled in the art, the registration module 70 may be an electronic module or a mechanical counter module with the same or essentially the same functionality.

The actuation mechanism 1 for actuating the canister 20 to deliver a dose of medicament is illustrated in FIGS. 4, 4a, 5, 5a, 6 and 6a. The actuation mechanism 1 operates to compress the canister body 22 relative to the valve stem 24 held in the nozzle block 62 to deliver a dose of medicament. The elements illustrated in FIGS. 4, 4a, 5, 5a, 6 and 6a are accommodated in the housing 10 and retained by the chassis 40 but both the housing 10 and the chassis 40 are removed from FIGS. 4, 4a, 5, 5a, 6 and 6a for clarity.

The structure of the actuation mechanism 1 is as follows.

The actuation mechanism 1 comprises loading means or a loading element 6 for loading the actuation mechanism 1 with an actuation force for compression of the canister to deliver a dose of medicament. A resilient loading element 6, such as a coiled spring is provided for the storage and release of the actuation force. The coiled spring 6 is movable in one direction substantially along the cylindrical axis of the canister 20 to store the actuation force, and in an opposite direction substantially along the cylindrical axis of the canister 20 to release the actuation force.

The coiled spring 6 is connected at its lower end to a yoke 4. The yoke 4 has a canister-engagement portion. A cover element 8 may engage the coiled spring 6 at its upper end. The cover element 8 may facilitate the spreading of the load on the coiled spring 6 into the housing 10 of the inhaler, and may also aid location of the coiled spring 6 within the housing.

Figure 2:
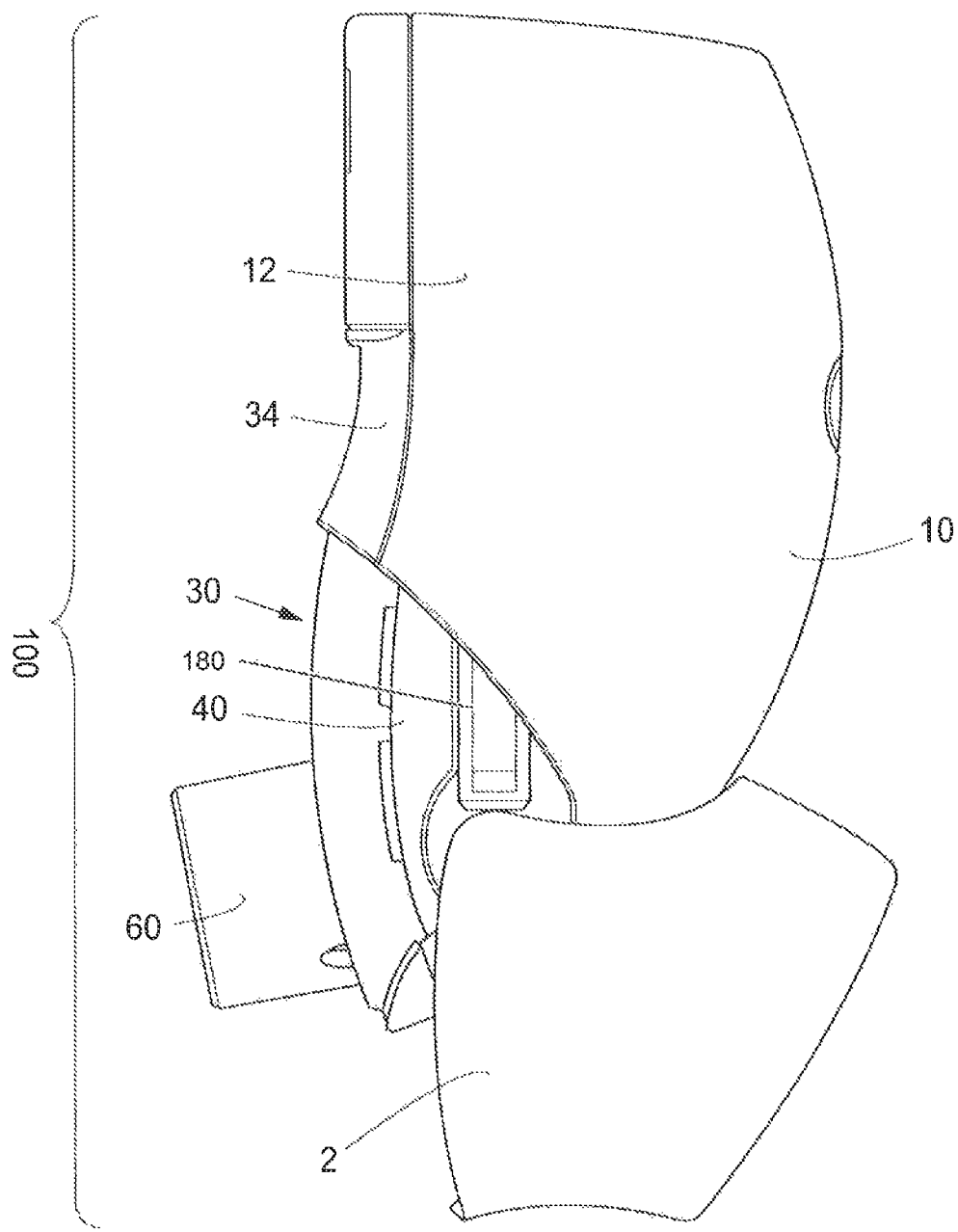
FIG. 2 is a side view of the inhaler of FIG. 1 with the actuating means in the open position.

As illustrated in FIGS. 1-3, the actuation locking means, in the present embodiment represented by the cover 2 is mounted for movement between a first, or open, position as relative to the housing 10, and a second, or closed, position relative to the housing 10. In the embodiment shown, the cover 2 is pivotally mounted on the chassis 40 and has a cam 110 at the pivot point 120. In this way, pivotal movement of the cover 2 to the first or open position allows the yoke 4 to move downwards, under the force applied by the coiled spring 6. Conversely, pivotal movement of the cover 2 to the second or closed position applies an upward force to the yoke 4 and forces it upwards, compressing the coiled spring 6. The yoke is thus moveable in a direction substantially along the cylindrical axis of the canister 20. As a result of the gearing inherent in the cam loading mechanism, the total distance that the yoke 4 performs in response to pivotal movement of the cover 2 is greater than the distance which the canister body 22 and the valve stem 24 of the canister 20 need to be compressed in order to release a dose of medicament.

The actuation mechanism 1 further includes a trigger mechanism 3 for holding the loading element 6 against compression of the canister 20. The trigger mechanism 3 is constructed as follows.

Figure 5:
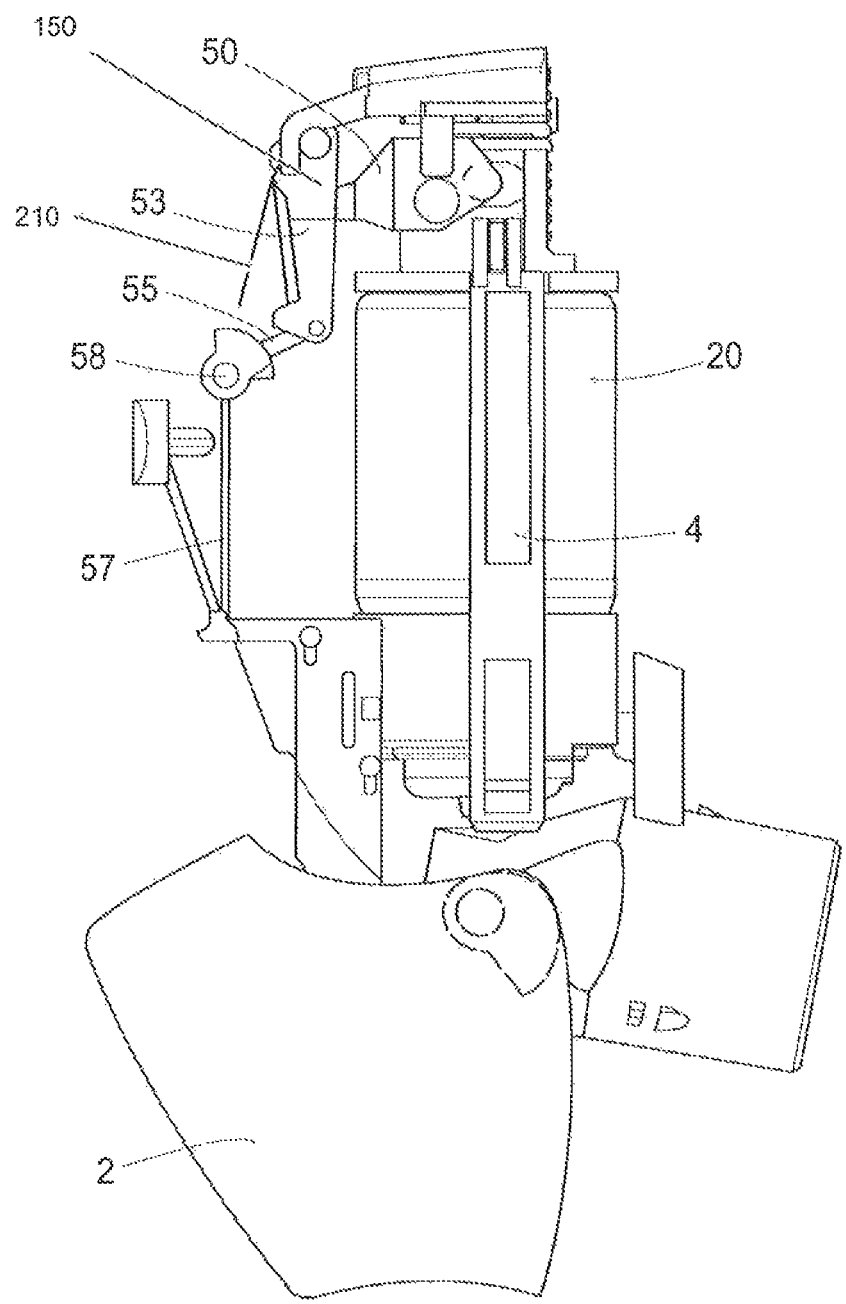
FIG. 5 is a schematic side view of the actuation mechanism of FIG. 4 in the armed or "charging" position.
Figure 5A:
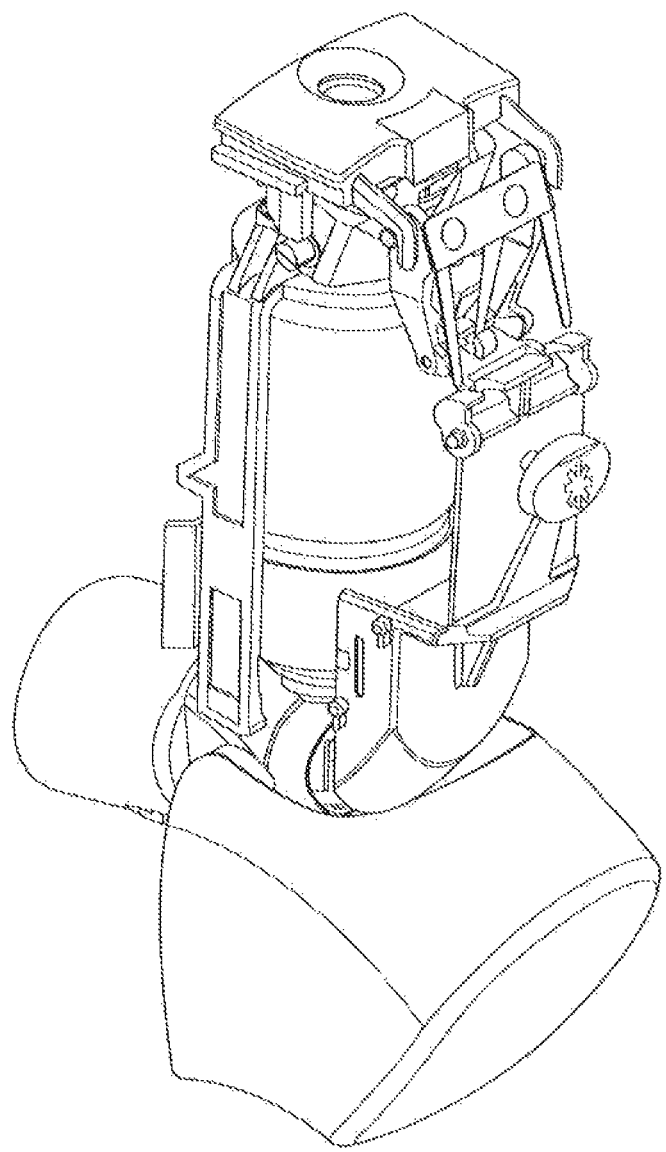
FIG. 5a is a corresponding perspective view of the actuation mechanism of FIG. 4 in the armed or "charging" position.

A yoke lever 50 (lever 50) is pivoted about lever hinge pins 130 that are arranged in mating hinge holes 132 in the chassis 40 and has a pair of lever arms 51 engaging the yoke 4 in a corresponding pair of horizontal yoke groves 140, whereby the lever 50 performs a pivotal movement when the yoke 4 is moved upwards or downwards. At the distal end from the arms 51, the lever 50 has yoke lever lock end in the form of a planar portion 52 that is arranged to engage a lock rib 150 on a lock member 53 (lever lock 53) when the lever lock 53 is in a locked position. The lever lock 53 is pivoted about lock hinge pins 160 that are arranged in mating hinge holes in the chassis 40. In its locked position, as illustrated in FIGS. 5 and 5a the lever lock 53 holds the loading means, via the lever 50, against compression of the canister 20.

The trigger mechanism further comprises latch means in the form of a release member (drop link element) 55 movable between a latch position arranged to store the actuation force to retain the canister 20 in the rest or charging position, and a latch-release position arranged to release the actuation force and allow compression of the canister 20. The drop link element 55 is pivotally connected at one end to the lever lock 53. The drop link 55 is provided at its other end with a latching element 56 adapted to engage a trigger element pivotally mounted on the chassis. The trigger element 57 is arranged for movement in response to inhalation by the user at the mouthpiece or manual depression by the user of a firing button, to cause actuation of the canister 20 to deliver a dose of medicament to the mouthpiece. In the embodiment shown, the firing button is made integral with an inlet duct cover 64. However, it may not be made integral therewith. The firing button 48 enables the user to deliver a dose of medicament as an emergency function if, for any reason, the usual actuation mechanism fails, or if the user cannot inhale significantly to activate the actuation mechanism to deliver a dose of medicament for example, during a chronic asthma attack. In the preferred embodiment, the trigger element 57 constitutes an inhalation responsive trigger vane that is an element, which is moved in response to and by a flow of air there over.

The latching element 56 contacts and rests upon the trigger vane 57 at its trigger pivot shaft 58 when the drop link 55 and trigger vane 57 are at their latch position.

Figure 6:
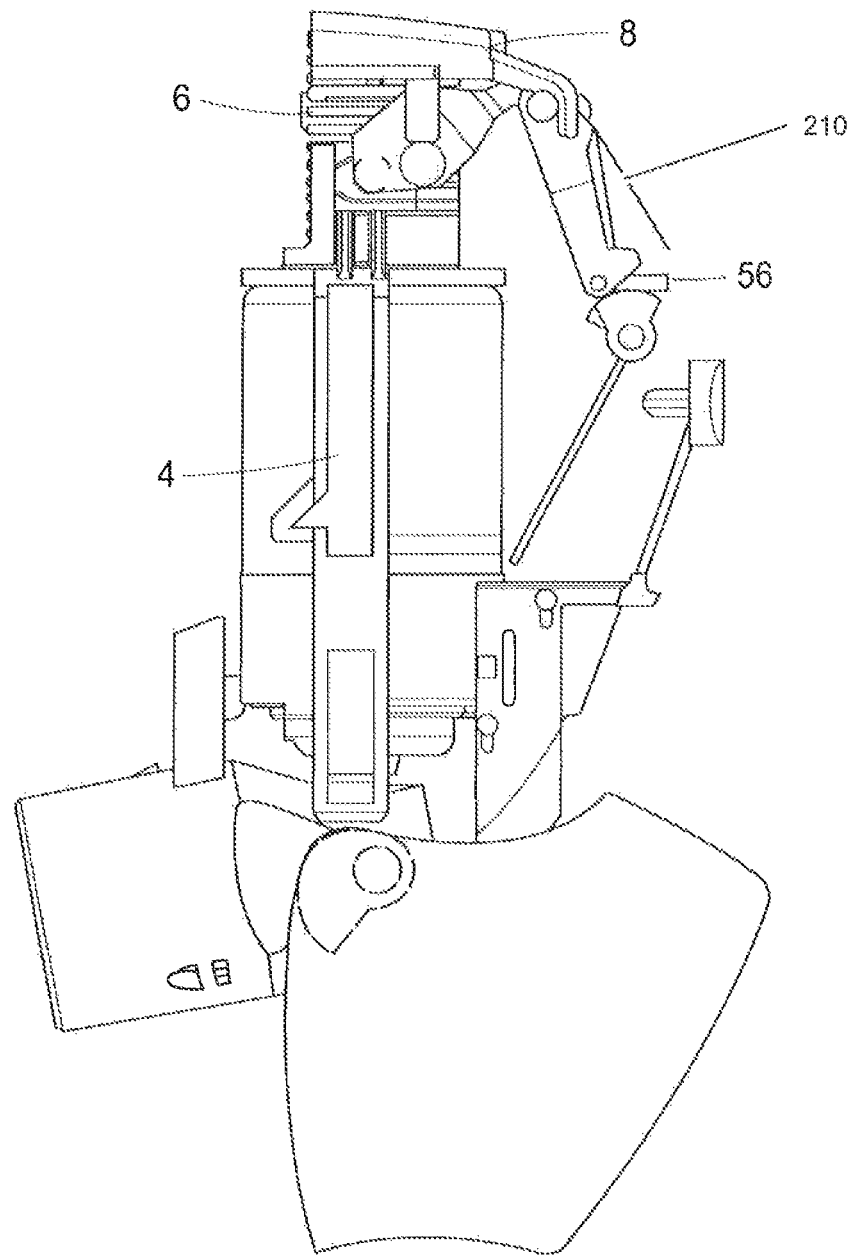
FIG. 6 is a schematic side view of the actuation mechanism of FIG. 4 in the triggered "medicament discharging" position.
Figure 6A:
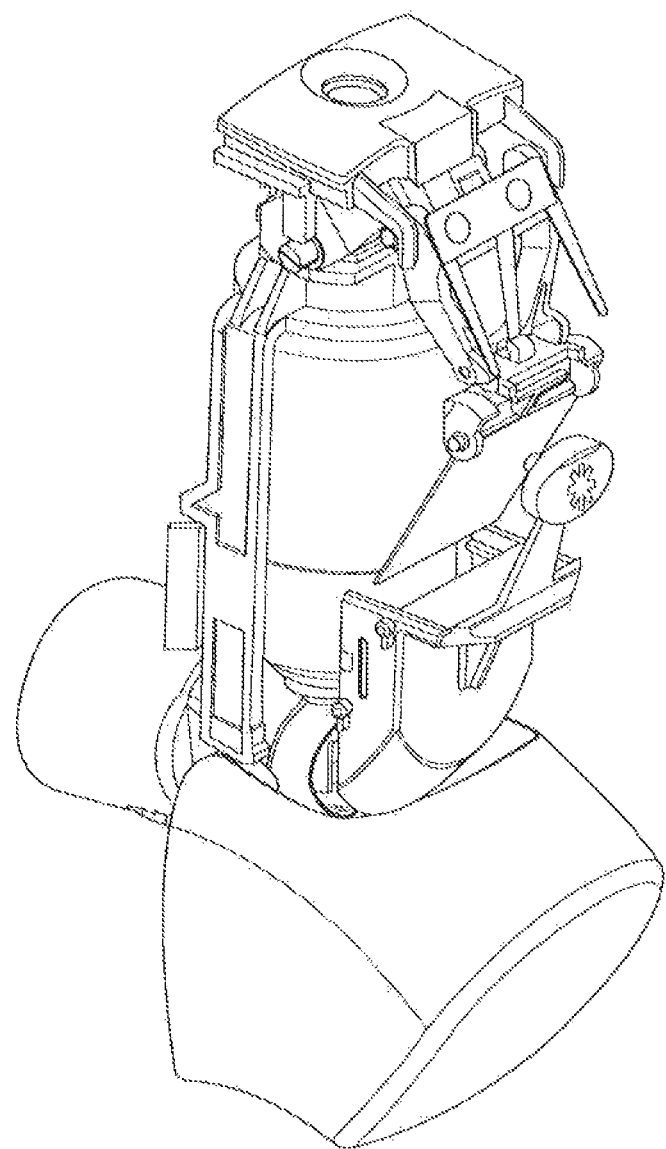
FIG. 6a is a corresponding perspective view of the actuation mechanism of FIG. 4 in the triggered "medicament discharging" position.
Figure 7:
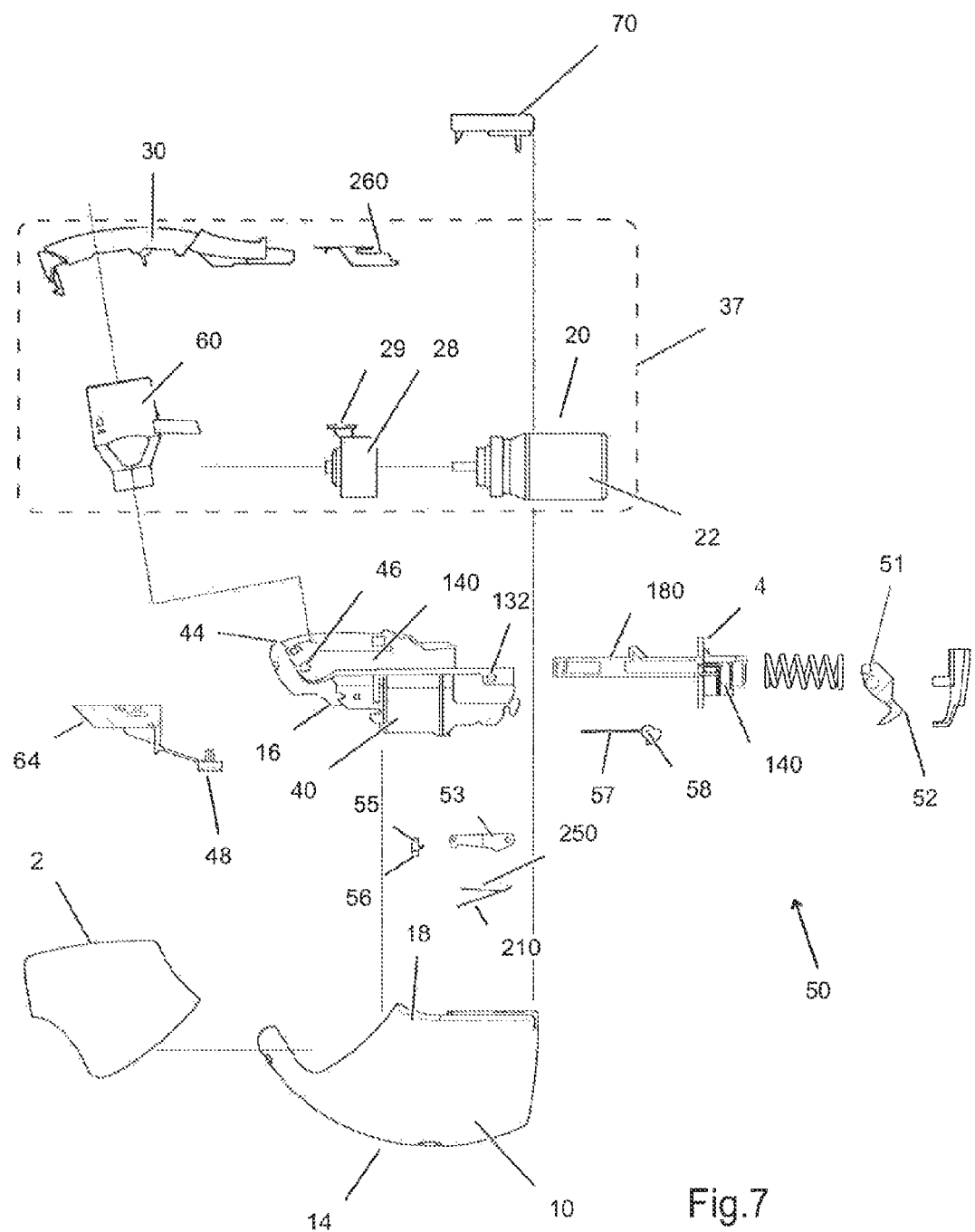
FIG. 7 is an exploded view of the components of the inhaler of FIG. 1 with an actuation mechanism of FIG. 4.

Operation of the actuation mechanism will now be described with reference to FIGS. 4-6 which illustrate the various parts of the actuation mechanism in schematic form for case of understanding.

Figure 4:
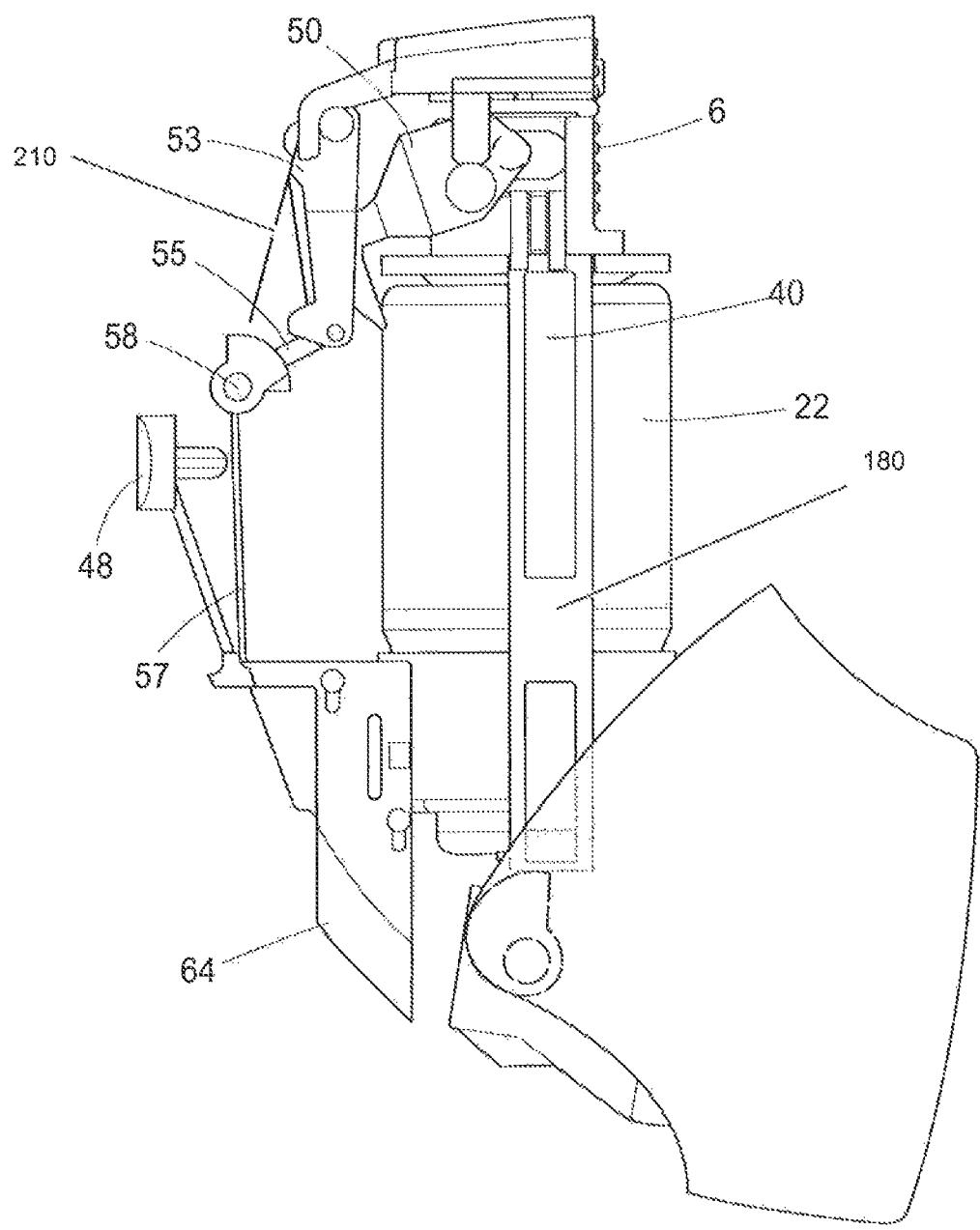
FIG. 4 is a schematic side view of one embodiment of an actuation mechanism in the neutral or "rest" position.
Figure 4A:
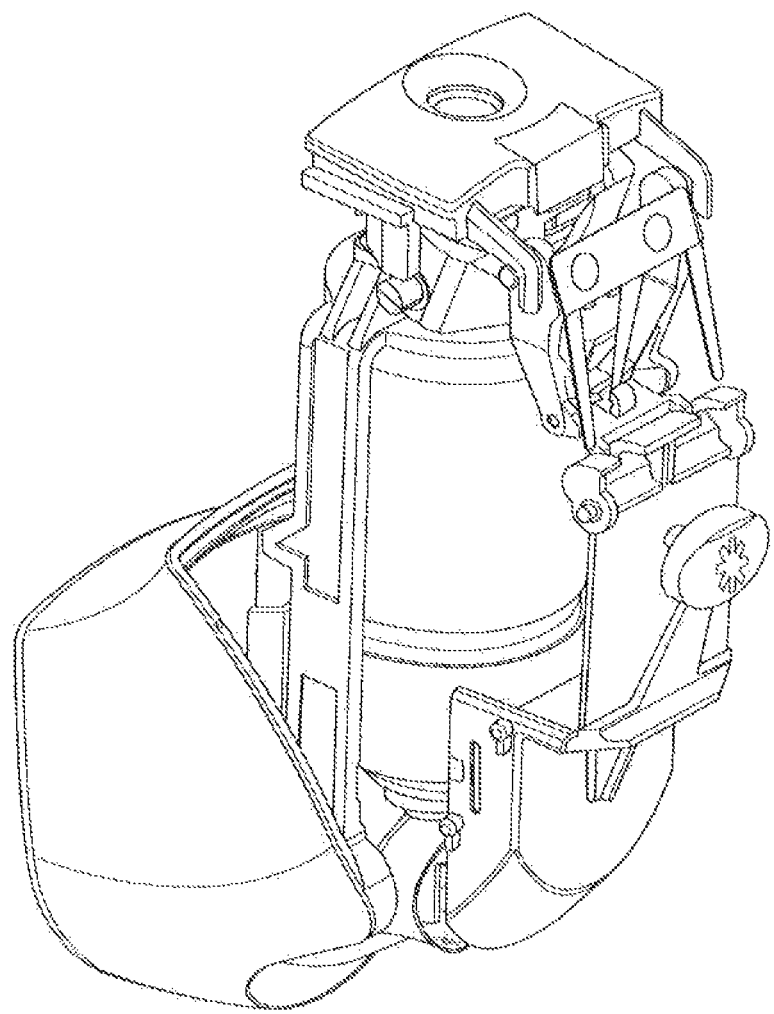
FIG. 4a is a corresponding perspective view of the actuation mechanism of FIG. 4 in the neutral or "rest" position.

FIG. 4 illustrates the neutral or "rest" position of the actuation mechanism in which the cover 2 encloses the mouthpiece when the inhaler 100 is not in use. The yoke 4 is in its uppermost position so that the coiled spring 6 is in a loaded state, thus storing an actuation force. All mechanical components of the inhaler but the yoke 4 are unloaded and there is no compression of the canister 20. An air gap exists between the canister engagement portion of the yoke 4 and the base of the canister 20. However, it can be envisaged that dampening means, such as a foam or rubber element, may be placed between the yoke 4 and the canister 20. The lever 50 and the lever lock 53 are both in their locked positions. The drop link 55 is in its latched position whereby the latching element 56 rests upon the pivot shaft 58 of the trigger element 57, thereby holding the lever lock 53 in its locked position.

When the inhaler 100 is to be used, the cover 2 is opened to access the mouthpiece, as shown in FIG. 5. Upon pivotal movement to open the cover 2, the yoke 4 is moved downwardly to engage the base of the canister 20. In this state, the coiled spring 6 biases compression of the canister 20 via the yoke 4, and the yoke 4 compresses the canister 20 relative to the valve stem a distance of about 0-2 mm. However, further compression of the canister 20 to deliver a dose of medicament is prevented by the load applied to the trigger mechanism. The lever lock 53 holds the loading means, via the lever 50, in its locked position, against compression of the canister 20. The lever 50 and the lever lock 53 remain in their locked position, the planar portion of the lever 50 being forced against the lock rib 150 on the lever lock 53. In this "armed" or charging state, inhaler 100 is loaded ready for the delivery of a dose of medicament.

Inhalation by the user at the mouthpiece causes air to flow through the air flow path defined inside the housing from the inlet opening to the mouthpiece. Due to the pressure drop created by the flow inside the housing 10 (or use of the firing button as previously described), the trigger element 57 is caused to pivot in a flow direction to its latch-release position illustrated in FIG. 6. Pivotal movement of the trigger element 57 to its latch release position causes the drop link 55 to pivot in an upwards direction to its release position. Pivotal movement of the drop link 55 in turn causes the latching element 56 to be lifted over and to disengage from the pivot shaft 58 of the trigger element 57. The pivot shaft 58 of the trigger element 57 may be substantially circular in cross section, however any shape may be envisaged, such as a sector of a circle, provided that upon rotation of the pivot shaft 58, there is sufficient surface provided to allow the latching element 56 to be lifted over and to disengage from the pivot shaft 58. The pivotal movement of the drop link 55 thus causes the lever lock 53 to pivot in the release direction from its locked or armed position to its release position, to allow compression of the canister by disengagement of the planar surface 52 from the rib. The lever 50 in its unlocked state allows compression of the canister 20 to deliver a dose of medicament under the biasing of the coiled spring 6. In this state the inhaler may be described as being in its "fired", "triggered" position or "medicament discharging position".

The lever lock 53 has a re-set spring 210 which forces it to pivot back and to return to its latching position. The droplink 55 uses another spring leg 250 of the same reset spring 210, however in this case the reset spring allows it to pivot back to return to a reset position ready to take up its latching position. In its reset position, the latching element 56 of the droplink element 55 abuts the pivot shaft 58 of the trigger element 57. Each of the re-set springs is made from a plastics material or metal. The provision of re-set springs ensures that both the trigger element 57 and the droplink 55 are ready to take up or return to their latch position, respectively, without reliance on gravitational force.

Closure of the cover 2 causes the yoke 4 to move upward, which has three effects. Firstly, it allows the canister 20 to reset itself. Secondly, it causes the lever 50 and the lever lock 53 to return to their locked position in the neutral position of the actuation mechanism illustrated in FIG. 4, and the droplink 56 to return its latch position. Thirdly, it stores the actuation force in the coiled spring 6, via the loading of the yoke 4, ready for when the inhaler 100 is to be used.

FIGS. 8a to 8f show a schematic embodiment of one embodiment of a breath actuated inhaler (BAI) actuator adapted to show the function of the actuation mechanism in detail. The BAI actuator 100 comprises a loading element 6, a breath actuated trigger mechanism 3 and actuation locking means 2.

The loading element 6 provides the force necessary for actuation of the metering valve of the canister, and needs therefore to be capable of being loaded with an actuation force of suitable magnitude. The actuation force required for actuation of the metering valve depends on the type of metering valve and, to some extent, on the type of triggering mechanism. In one embodiment the loading element 6 may be integrated in the metering valve, thus excluding the need for a separate loading element. In FIGS. 8a to 8f the loading element 6 is illustrated as a coiled spring, but it may be of any suitable type that is capable of being loaded with the required actuation force.

The breath actuated (BA) trigger mechanism 3 is arranged to counteract the actuation force of the loading element 6 and to fire the actuator 100 by releasing the actuation force of the loading element 6 in response to an inhalation breath. One example of a BA trigger mechanism is disclosed in detail below, but there are many other types of BA trigger mechanisms that can be used in the present BAI actuator. One example is a mechanism of catch member type, wherein a trigger element is arranged to release a catch member in response to a breath flow. Another example is a mechanism of bistable pivot joint type, wherein a trigger element is pivotal between an armed position wherein it counteracts the actuation force via a pivot joint restricted to a joint angle close to, but less than, 180° and a fired position, wherein the trigger element is arranged to pivot the joint angle beyond 180° in response to a breath flow, thereby releasing the actuation force. But other mechanisms or combinations thereof may also be used.

As mentioned above, many components in the trigger mechanism are small sized and often made of plastic material and therefore susceptible to material creep upon prolonged loading. Therefore, the actuator is provided with actuation locking means 2 moveable between a locked position (FIG. 8f) wherein it relieves the actuation force from the trigger mechanism setting the trigger mechanism 3 in a neutral or unloaded position, and an armed position (FIG. 8a) wherein the trigger mechanism 3 is set in an armed position. In the disclosed embodiment, the actuation locking means 2 is further arranged to function as actuating means that are arranged to load the loading element 6 with actuation force upon movement from its armed position to its locked position (FIGS. 8d and 8e), after the actuator is fired. According to one embodiment, not shown in figure, the actuation locking means 2 is provided separately from the actuating means.

Figure 8A:
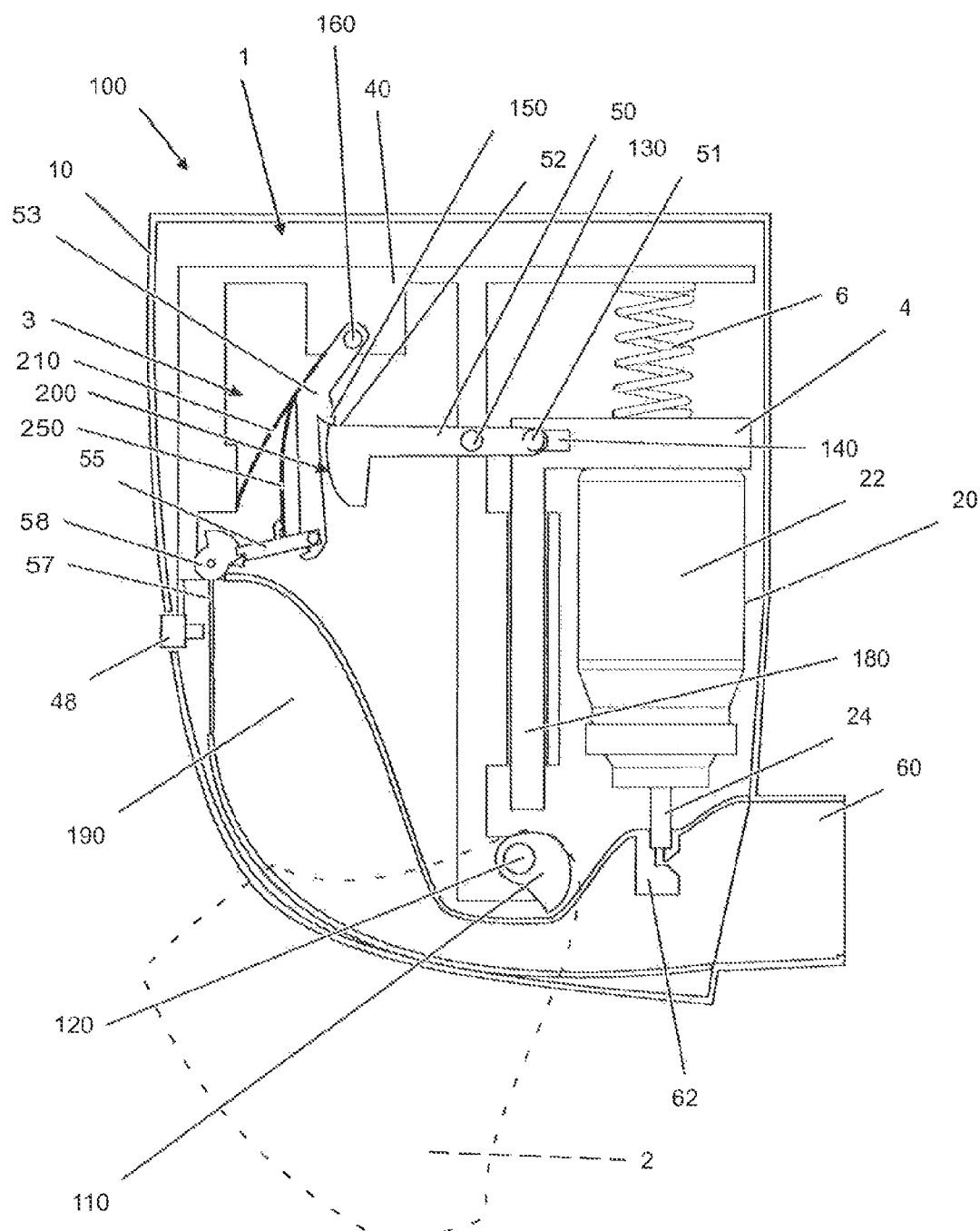
FIGS. 8a to 8f show schematic side views of a number of states of operation for an embodiment of a breath actuated inhaler (BAI) actuator, with a schematic actuation mechanism.

In the disclosed embodiment the actuation locking means 2 is formed as a pivotal lever with a helical cam member 110 arranged about a pivotal point 120. Upon movement of the locking means 2 after the actuator is fired, from its armed position (FIG. 8c) to its locked position (FIG. 8f), the helical cam member 110 acts on a loading yoke 4, initially to load the loading element 6 with actuation force (FIGS. 8d and 8e) and to arm the trigger mechanism 3 (FIG. 8e), and subsequently to overload the loading element to relieve the actuation force from the trigger mechanism 3 setting it in a neutral or unloaded position (FIG. 8f). Upon subsequent movement of the locking means 2 from its locked position to its armed position, the helical cam member 110 initially acts on the loading yoke 4 to unload the overloading force on the loading element 6 to arm the trigger mechanism, where after it is moved to its armed position, wherein the helical cam is in a position that allows firing of the actuator (FIG. 8a).

According to one embodiment, the helical can member 110 is formed so that the actuation locking means 2 is retained in the locked position by the actuation force of the loading element 6. In the disclosed embodiment, the helical cam member is formed so that the active section 170 that is in contact with the yoke 4 is either flat or inclined so that the actuation force gives rise to a stable state or that the actuation locking means 2 is urged in the locked direction. In the disclosed embodiment, the actuation locking means 2 is formed as a protective cover 2 arranged to limit the access to the mouth piece 60 in its locked position and to allow access to the same in its armed position.

In the disclosed embodiment, the BAI actuator is arranged for actuation of a compression firing canister of the type disclosed more in detail above. However, according to other embodiments, the BAI actuator may be arranged for actuation of canisters with other types of metering valves, such as valves that fire upon withdrawal of a control stem, rotary type valves and the like. Moreover, according to one embodiment, the metering valve may be of a type that is biased in the firing direction, and in such case, the biasing force of the metering valve, may be used in lieu of or in combination with the loading element 6.

In the disclosed embodiment, the loading element 6 is arranged to act on the canister body 22 of the canister 20, and the actuation involves depressing the canister body 22 of the canister with respect to a static nozzle block 62. In another embodiment, not disclosed in the figures, the loading element 6 is arranged to act on a moveable nozzle block, wherein actuation involves translation of the nozzle block with respect to the canister body 22 of the canister 20 to depress the valve stem 24.

According to one embodiment the loading element 6 is arranged to act on the non valve end of the canister body 22 arranged in the BAI actuator 100, via the yoke 4. In the disclosed embodiment, the loading element 6 is a coiled spring arranged in alignment with the actuation direction of the canister 20. The yoke 4 comprises two cam follower legs 180 for cam interaction with, and transmission of, loading translation from the helical cam 110 to the loading element 6. According to one embodiment, as is exemplified by the embodiment of FIGS. 1 to 7, the cam follower legs 180 are arranged to extend along diametrically opposite sides of the canister 20, whereby the force transmitted from the actuation locking means 2 via the helical cam 110 to the loading element 6 is aligned with actuation direction of the canister 20. In the embodiment of FIGS. 8a to 8f, the yoke 4 comprises two cam follower legs 180 that are parallel, but not diametrically arranged with respect to the canister 20, mainly in order to make the figure clearer, but also in order to show that the cam follower legs 180 need not to be in perfect alignment with the actuation direction of the canister.

According to one embodiment, the trigger mechanism 3, the yoke 4 and the actuation locking means 2, are supported by a chassis 40 arranged in an external housing 10. As mentioned above, the chassis gives rigidity to the actuator, and by supporting all moveable parts by the chassis 40 problems relating to tolerances between different parts are reduced. In FIGS. 8a to 8f the chassis 40 is reduced to a strict illustrative design, to make the function of the actuation mechanism 1 clearer, whereas the embodiment shown in FIGS. 1 to 7 comprises a chassis 40 that allows a more compact and load efficient design. In the disclosed embodiments, the cam follower legs 180 are arranged for and limited to linear movement in mating yoke grooves 140 formed in the chassis 40.

FIGS. 8a to 8f show one embodiment of a trigger mechanism comprising:
- a yoke lever 50 arranged to transform the movement of the yoke 4 to a pivotal movement of a lock end 52 thereof,
- a lock member 53 pivotally moveable between an armed position (FIG. 8a) wherein it is arranged to prevent further pivotal movement of the yoke lever lock end 52 in the actuation direction, and an open position wherein the yoke lever 50 is free to move beyond the armed position in the actuation direction, in the armed position the lock member 53 is biased towards the open position by the yoke lever 52 which in turn is biased in the actuation direction by the loading element 6 via the yoke 4,
- a trigger element 57 arranged for movement in response to an inhalation breath, and
- a release member 55 arranged between the lock member 53 and the trigger element 57 to hold the lock member 53 in the armed position, and to release the lock member 53 in response to movement of the trigger element 57.

The yoke lever 50 is pivotally supported by the chassis 40 by lever hinge pins 130 or the like, and comprises lever arms 51 that are arranged to engage corresponding yoke grooves 140 formed in the yoke 4. The yoke lever 50 is formed to create a lever effect gearing down the force applied on the components in the triggering mechanism from the loading element 6. The gearing is achieved in that the longitudinal distance between the hinge pivot point 130 and the lever arms 51 is shorter than the distance between the hinge pivot point 130 and the yoke lever lock end 52. In the disclosed embodiment, the yoke lever 50 is arranged so that the lock end 52 performs an upward movement when the yoke 4 moves downwards, but in an alternative embodiment the yoke lever 50 may be formed to reverse the direction of movement by arranging the lever arms 51 in between the hinge pivot point 130 and the lever lock end 52. In the later case, the other parts of the trigger mechanism must be adapted to the reversed direction of movement.

In the disclosed embodiment, the lock member 53 is pivotally supported by the chassis by lock hinge pins 160. The lock member 53 comprises a lock rib 150 arranged to act as a catch member for the lock end 52 of the yoke lever 50 to arm the triggering mechanism. The pivot point 160 of the lock member 53, and the interaction between the lock rib and the lock end 52 of the yoke lever 50 are arranged so that the lock member 53 is biased towards the open position by the yoke lever 50. By designing this interaction properly a suitable gear down effect is achieved, reducing the force applied on the components of the trigger mechanism even further. A spring element 210 biases the lock member 53 in the closing direction, towards the yoke lever 50, in order to reset the trigger mechanism during loading of the actuation mechanism, as is shown in FIG. 8d. The yoke lever 50 comprises a lock member guide surface 200 at the lock end thereof. As is shown in FIG. 8c, the lock member guide surface 200 interacts with the lock rib 150 to hold the lock member in the open position when the actuator is unloaded.

The trigger element 57 is arranged at one end of an air flow duct 190 extending from the mouth piece 60 at the other end. The air flow duct 190 may be formed by the actuator housing 10, the chassis 40, or a combination thereof, and optionally with additional components. According to one embodiment, the trigger element is a pivotal vane with a trigger pivot shaft 58 that is pivotally supported by the chassis 40 at a trigger pivotal point and arranged to pivot about a the pivot axis in response to an air flow in the flow duct, e.g. an inhalation breath. The release member 55 is, at one end, pivotally connected to the lock member at a release pivot point 240, and at the other end it is arranged to interact with the trigger pivot shaft 58 to hold the lock member 53 in the armed position, and to release the lock member 53 in response to pivotal movement of the trigger pivot shaft 58. According to one embodiment, the release member 55 is a drop link element.

Figure 10A:
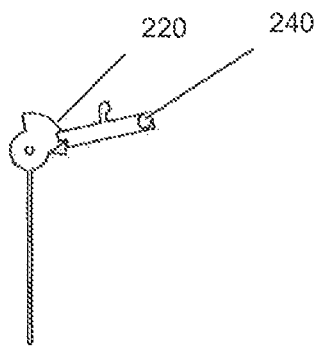
FIGS. 10a and 10b show perspective views of one embodiment of a release member and a trigger element of a trigger mechanism.
Figure 10B:
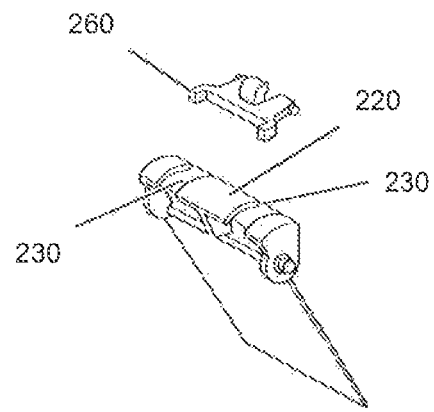
Figure 11A:
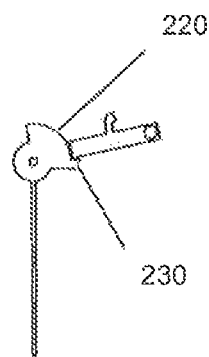
FIGS. 11a and 11b show perspective views of another embodiment of a release member and a trigger element of a trigger mechanism.
Figure 11B:
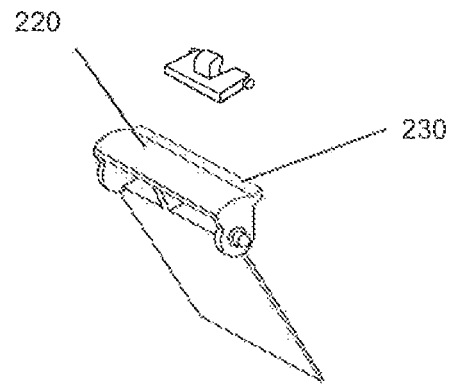

FIGS. 10*a*, 10*b*, 11*a* and 11*b* show two embodiments of trigger vane and release member combinations. The trigger pivot shaft 58 comprises an essentially semi cylindrical shaped release surface 220, and stop means 230 that ensure that the release member 55 enters the correct armed position upon arming the triggering mechanism 3. As mentioned above, the release member 55 is biased in the direction of the trigger pivot shaft 58 by the lock member 53, which in turn is biased in the opening direction by the loading element 6 via the yoke lever 50. In the armed position (FIG. 8*a*), the release member 55 is arranged to apply the biasing force in a direction that is essentially radial to the trigger pivot axis 58. When the trigger vane 57 is pivoted by an air flow in the air flow duct 190, the interaction end of the release member 55 rotates together with the trigger pivot shaft 58, and the direction of the biasing force is shifted (lifted) from the trigger pivot axis 58 (FIG. 8*b*), and upon sufficient rotation the shifted biasing force makes the release member 55 detach from its armed state whereby the actuator is fired (FIG. 8*c*). In FIGS. 10*a* and 10*b*, stop means 230 of the trigger pivot shaft 58 are provided on both sides of a semi cylindrical release surface 220, and the corresponding release member comprises two stop protrusions 260 that are arranged to abut the stop means 230 of the trigger element. In FIGS. 11*a* and 11*b* the support means is formed by a stop ridge 230 at the lower end of the release surface 220. Moreover, the stop means 230, ensures that the release member 55 rotates together with the trigger pivot shaft 58. In order for the release member 55 to return to the armed position resting upon the trigger pivot shaft 58 upon loading of the actuator mechanism 1, a reset spring member 250 is arranged to bias the release member 55 in the downwards direction (FIG. 8*e*).

FIGS. 8*a* to 8*f* schematically shows the BAI actuator in different states of operation, wherein:

FIG. 8*a* illustrates the armed state, when the actuator is ready to be fired by an inhalation breath (FIGS. 8*b* and 8*c*) or by use of the firing button 48. The protective cover 2 which functions as loading means and actuation locking means is in its open or armed position whereby the actuation mechanism is able to be fired. As is discussed in detail above, the loading element 6 is loaded with an actuation force that exceeds the reset bias force in the metering valve of the canister 20, and the triggering mechanism 3 counteracts the actuation force via the yoke 4.

Figure 8B:
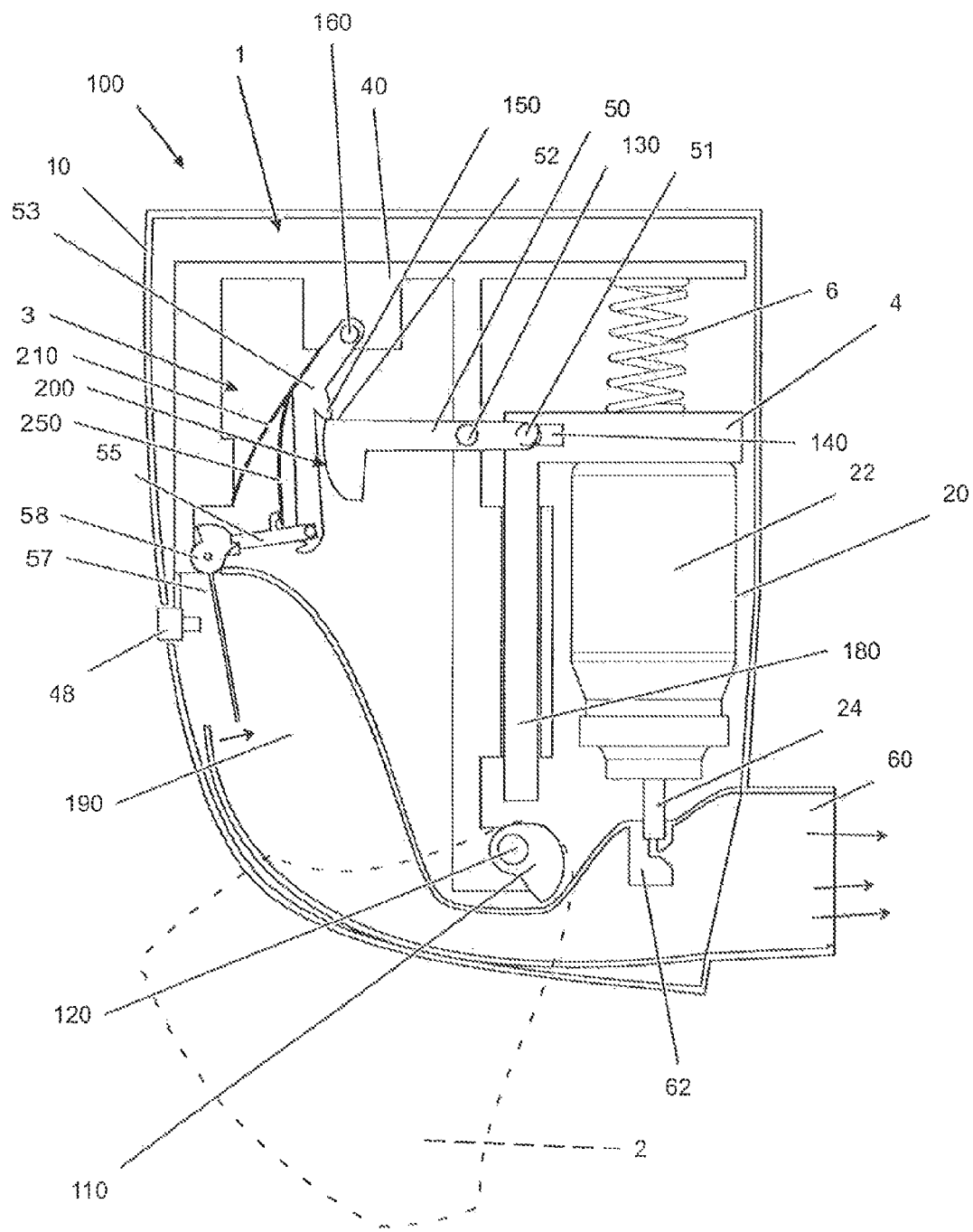
Figure 8C:
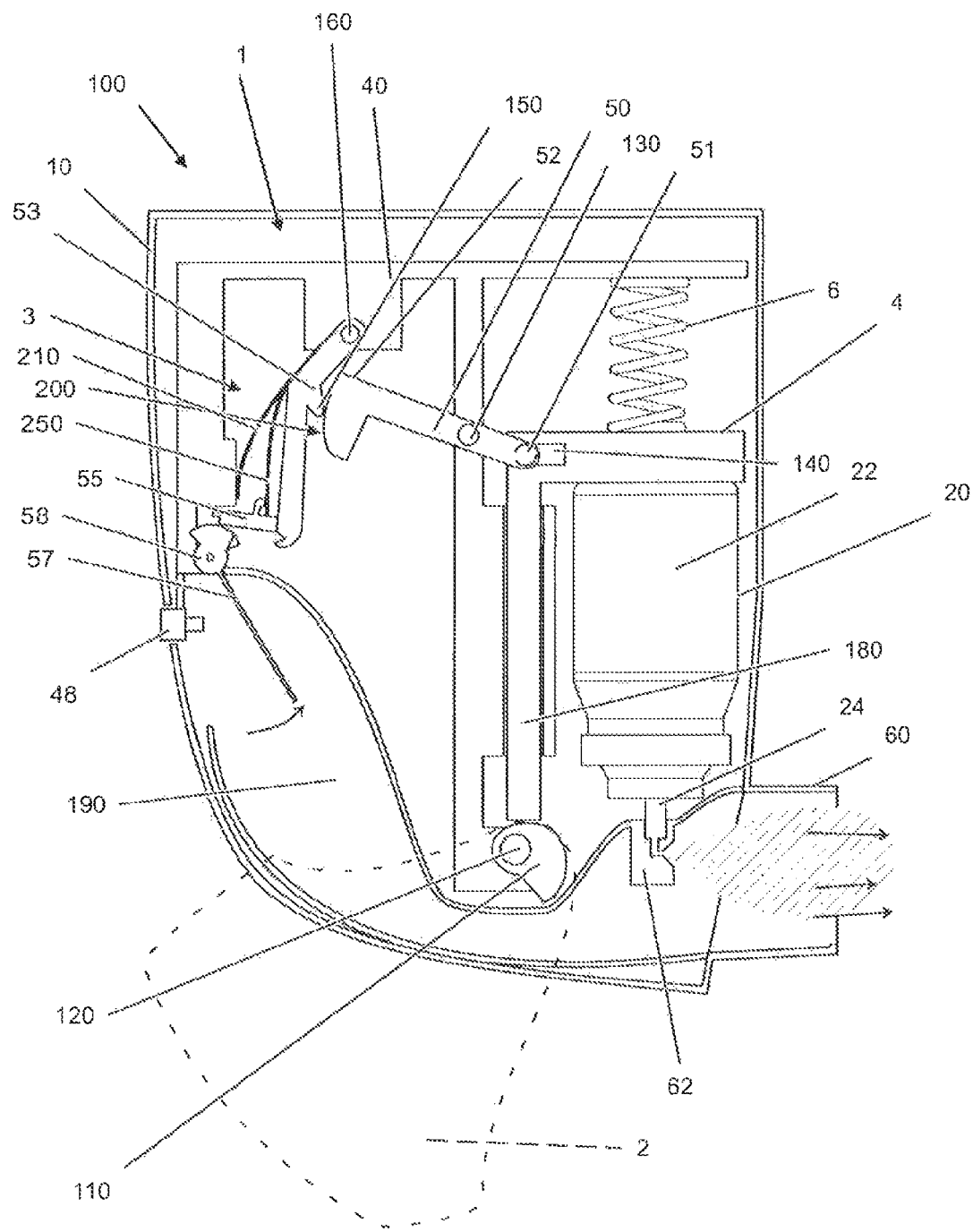
Figure 8D:
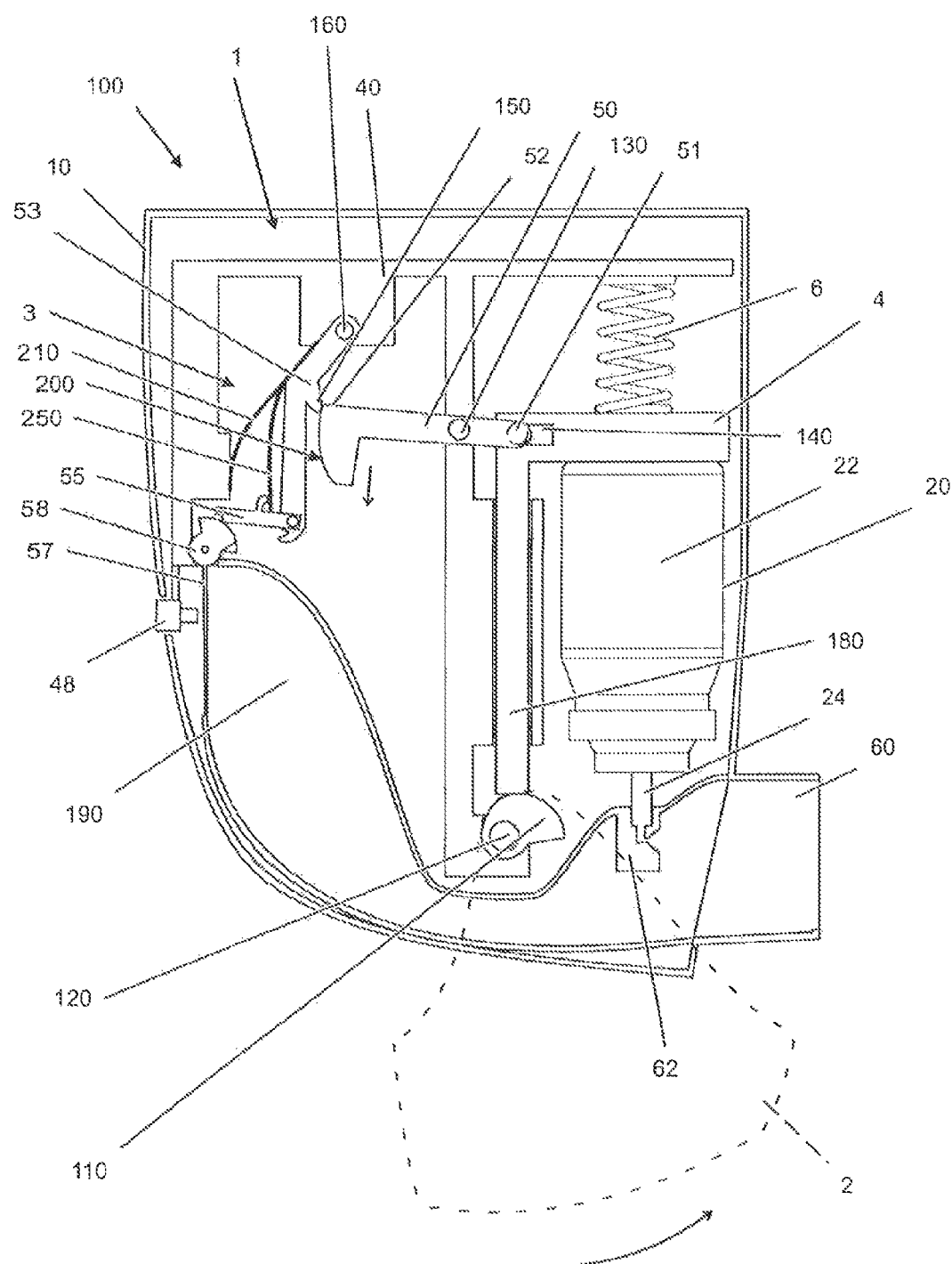
Figure 8E:
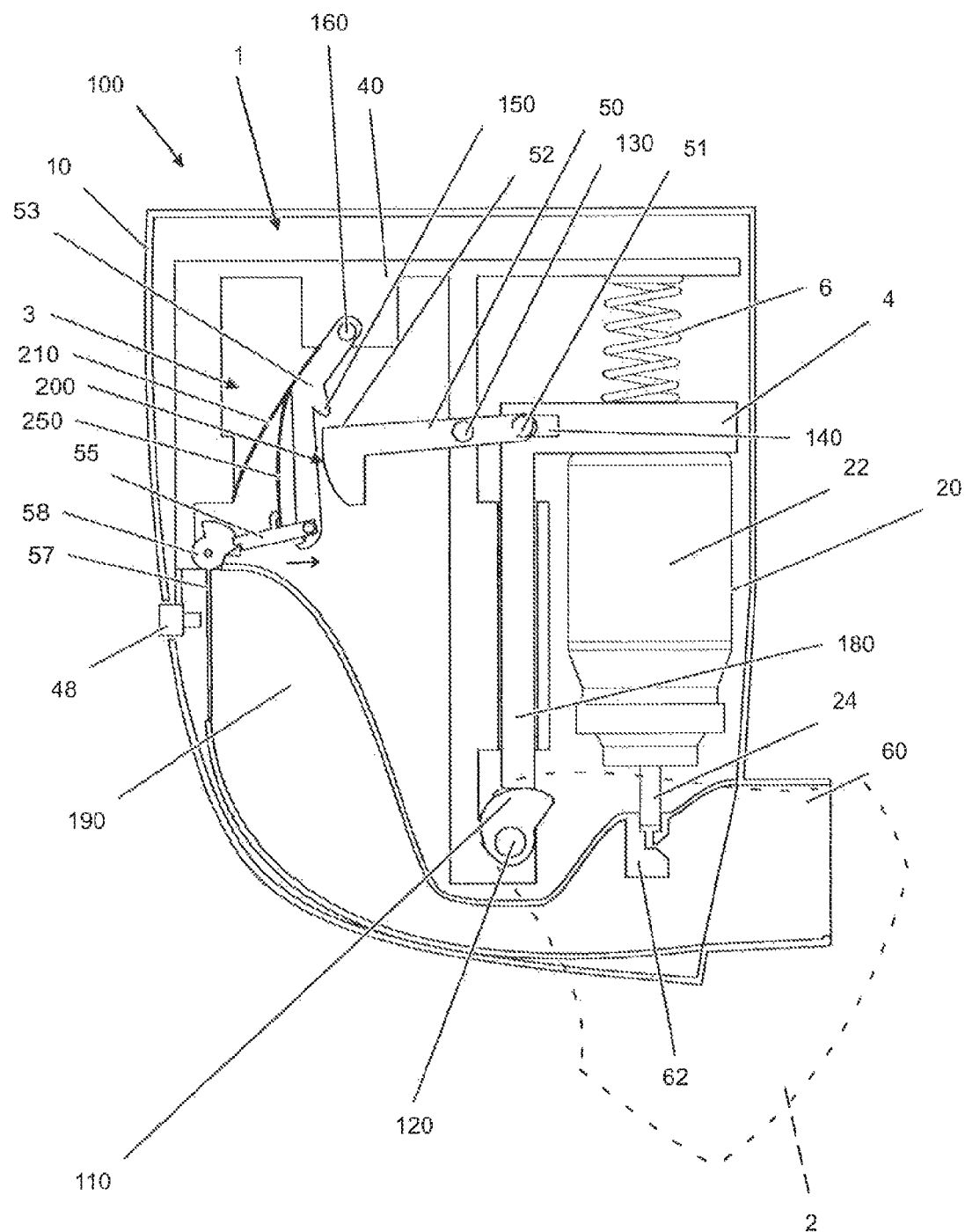
Figure 8F:
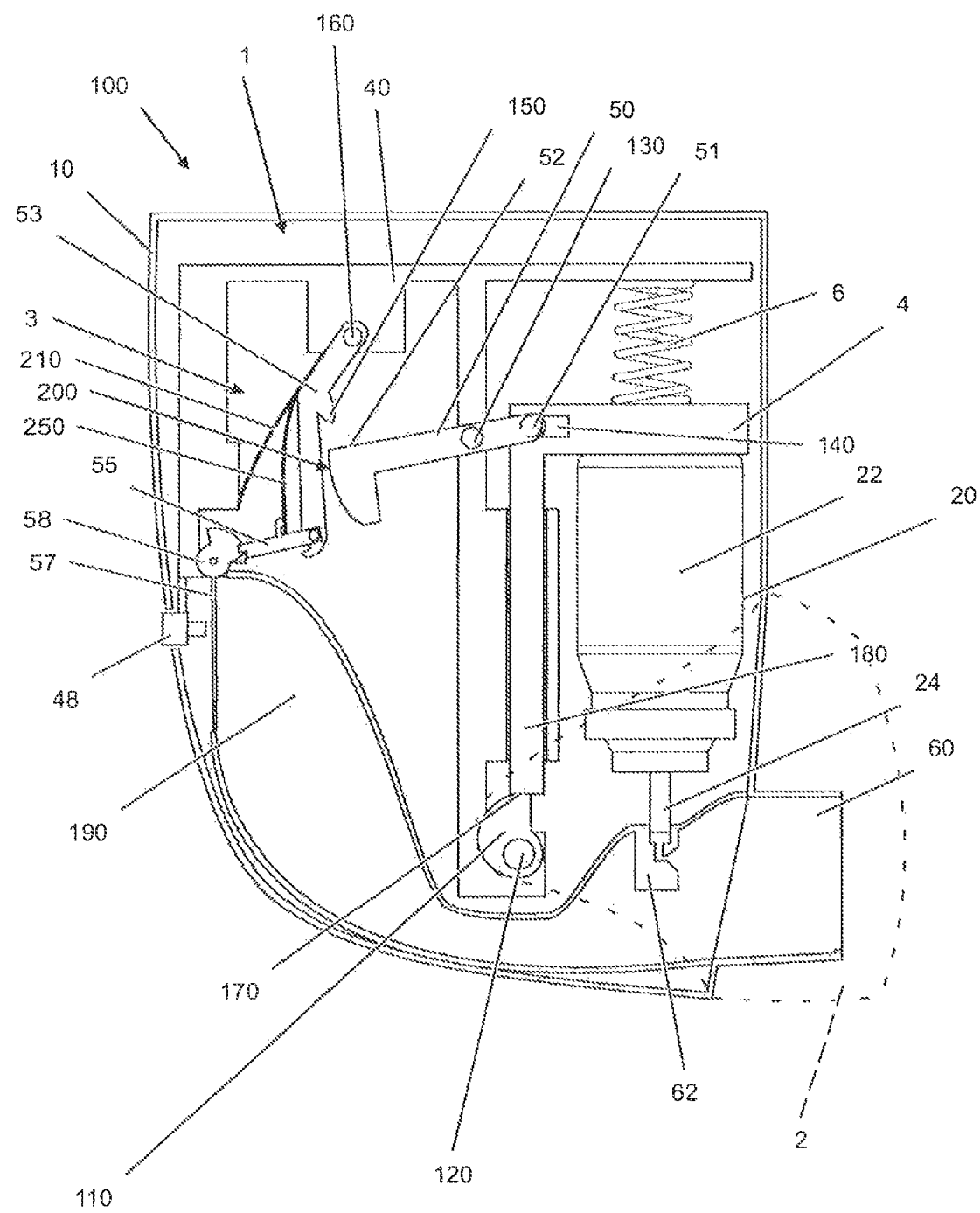
Figure 9:
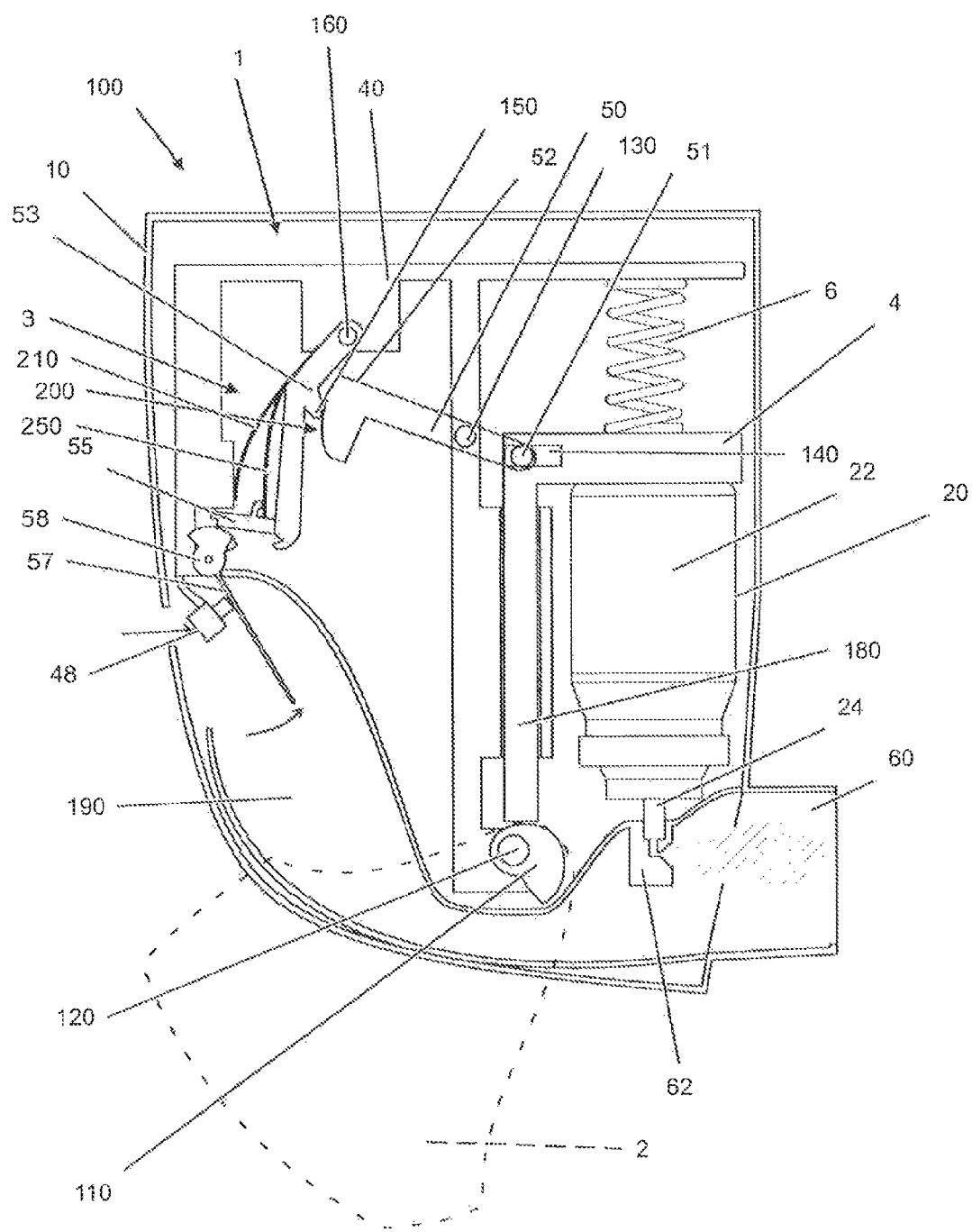
FIG. 9 shows an alternative actuation mode for the BAI actuator according to FIGS. 8a to 8f.

FIG. 8*b* illustrates an initial phase of a firing of the actuator by an inhalation breath, wherein the trigger vane 57 is pivoted an amount, but the release member 55 is still in locking contact with the trigger pivot shaft 58 and thus prevents firing of the actuator.

FIG. 8*c* illustrates the fired state, wherein the trigger vane 57 is further pivoted and the release member 55 has been detached from the pivot shaft 58 and the lock member 53 is pivoted to release the yoke lever 50 whereby the actuation force is released and the canister 20 is depressed to fire a dose of medicament into the inhalation air flow through the mouth piece 60.

FIG. 8*d* illustrates the process of loading the loading element 6 and arming of the trigger mechanism 3. The protective cover 2 is pivoted in the closing direction, whereby the helical cam 110 forces the yoke 4 in the loading direction and the yoke lever 50 is pivoted in the armed direction. The lock rib 150 of the lock member 53 follows the guide surface 200 of the yoke lever 50, biased by the spring element 210.

FIG. 8*e* illustrates a state wherein the protective cover 2 is further pivoted in the closing direction, whereby loading element is essentially fully loaded, and the triggering mechanism has entered its armed state.

FIG. 8*f* illustrates the locked state of the actuation mechanism, with the protective cover 2 closed and wherein the helical cam 110 is arranged to "over load" the loading element 6 via the yoke 4, whereby the trigger mechanism is unloaded, referred to as the neutral position.

In order to fire the actuator 100, the cover is pivoted back to the initial state as is illustrated in FIG. 8*a*.

The invention claimed is:

1. An inhaler, comprising:
a chassis configured to receive a canister containing a medicament;
a trigger element moveably coupled to the chassis and configured to move to initiate firing of the canister;
a droplink moveable relative to the trigger element;
a lever lock hingedly coupled to the droplink; and
a lock spring configured to bias the droplink and the lever lock relative to the chassis;
a yoke lever moveably coupled to the chassis, wherein the yoke lever is moveable relative to the lever lock; and
a loading element configured to bias the canister relative to the chassis, wherein the yoke lever is moveably coupled to the loading element and the loading element is configured to move to fire the canister.

2. The inhaler of claim 1, wherein the trigger element is rotationally coupled to the chassis.

3. The inhaler of claim 1, wherein the lever lock is rotationally coupled to the chassis.

4. The inhaler of claim 1, wherein the lock spring is configured to bias the droplink relative to the lever lock.

5. The inhaler of claim 4, wherein the lock spring is configured to bias the lever lock relative to the chassis.

6. The inhaler of claim 1, wherein the droplink is releasably coupled to the trigger element.

7. The inhaler of claim 1, wherein the lever lock is releasably coupled to the yoke lever.

8. The inhaler of claim 1, further including a yoke moveably coupled to the yoke lever and configured to move to bias the loading element.

9. The inhaler of claim 1, wherein the lever lock includes a rib configured to releasably couple to an end of the yoke lever.

10. The inhaler of claim 9, wherein the rib includes a flat surface configured to releasably couple to a corresponding flat surface of the yoke lever.

11. An inhaler, comprising:
a chassis configured to receive a canister containing a pressurized medicament;
a trigger element rotatably coupled to the chassis and configured to rotate in response to an inhalation;
a droplink slideably coupled to the trigger element;
a lever lock rotatably coupled to the droplink and rotatably coupled to the chassis; and
a lock spring configured to bias the droplink relative to the lever lock;

a yoke lever rotatably coupled to the chassis, wherein the yoke lever is slideably coupled to the lever lock; and a loading element configured to bias the canister relative to the chassis, wherein the yoke lever is configured to move to release the loading element to fire the canister.

12. The inhaler of claim 11, wherein the lever lock is pivotally connected to the droplink.

13. The inhaler of claim 11, wherein the lock spring is configured to bias the lever lock relative to the chassis.

14. The inhaler of claim 11, wherein the droplink is releasably coupled to the trigger element.

15. The inhaler of claim 11, wherein the lever lock is releasably coupled to the yoke lever.

16. The inhaler of claim 11, wherein the lever lock includes a rib configured to releasably couple to an end of the yoke lever.

17. The inhaler of claim 16, wherein the rib has a flat surface configured to transmit a compressive force to a corresponding flat surface of the end of the yoke lever.

18. The inhaler of claim 17, wherein the flat surface of the rib is slideable relative to the corresponding flat surface of the end of the yoke lever.

* * * * *